US006761914B2

(12) United States Patent
Deckers et al.

(10) Patent No.: US 6,761,914 B2
(45) Date of Patent: *Jul. 13, 2004

(54) IMMUNOGENIC FORMULATIONS COMPRISING OIL BODIES

(75) Inventors: Harm M. Deckers, Alberta (CA); Gijs van Rooijen, Alberta (CA); Joseph Boothe, Alberta (CA); Janis Goll, Alberta (CA); Maurice M. Moloney, Alberta (CA); Anthony B. Schryvers, Alberta (CA); Joenel Alcantara, Alberta (CA); Wendy A. Hutchins, Alberta (CA)

(73) Assignee: SemBioSys Genetics Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/880,901

(22) Filed: Jun. 15, 2001

(65) Prior Publication Data

US 2002/0071846 A1 Jun. 13, 2002

Related U.S. Application Data

(63) Continuation-in-part of application No. 09/577,147, filed on May 24, 2000, now Pat. No. 6,372,234, which is a continuation-in-part of application No. 09/448,600, filed on Nov. 24, 1999, now Pat. No. 6,183,762, which is a continuation-in-part of application No. 09/084,777, filed on May 27, 1998, now Pat. No. 6,146,645.
(60) Provisional application No. 60/075,863, filed on Feb. 25, 1998, provisional application No. 60/075,864, filed on Feb. 25, 1998, provisional application No. 60/047,779, filed on May 28, 1997, provisional application No. 60/047,753, filed on May 27, 1997, and provisional application No. 60/212,130, filed on Jun. 16, 2000.

(51) Int. Cl.$^7$ .................. A61K 45/00; A61K 47/44; A61K 35/78; A61K 39/385; A61K 39/395
(52) U.S. Cl. ................ 424/776; 424/278.1; 424/283.1; 424/400; 424/725; 424/731; 424/757; 424/758; 424/768; 424/776; 424/812; 514/885
(58) Field of Search ............................ 424/400, 278.1, 424/283.1, 812, 725, 731, 757, 758, 768, 776; 514/885

(56) References Cited

U.S. PATENT DOCUMENTS

| | | |
|---|---|---|
| 3,971,856 A | 7/1976 | Daftary |
| 4,025,658 A | 5/1977 | Pominski et al. |
| 4,088,795 A | 5/1978 | Goodnight, Jr. et al. |
| 4,196,191 A * | 4/1980 | Almeida et al. ............ 424/450 |
| 4,362,759 A | 12/1982 | Harris |
| 5,602,183 A | 2/1997 | Martin et al. |
| 5,643,583 A | 7/1997 | Voultoury et al. |
| 5,683,710 A | 11/1997 | Akemi et al. |
| 5,683,740 A | 11/1997 | Voultoury et al. |
| 5,856,452 A | 1/1999 | Moloney et al. |
| 5,948,682 A | 9/1999 | Moloney |

FOREIGN PATENT DOCUMENTS

| | | |
|---|---|---|
| WO | WO 96/21029 A1 | 7/1996 |
| WO | WO 96/41543 | 12/1996 |
| WO | WO 98/27115 | 6/1998 |
| WO | WO 98/53698 A1 | 12/1998 |

OTHER PUBLICATIONS

Aguilar, C. et al., "Rheological Behavior of Processed Mustard. I. Effect of Milling Treatment", Journal of Texture Studies 22(1):59–84 (1991), pp. 85–103.

Armentia, A. et al., "In vivo allergenic activities of eleven purified members of a major allergen family from wheat and barley flour", Clinical and Experimental Allergy, 1993, vol. 23, pp. 410–415.

Cater, Carl M. et al., "Aqueous Extraction–An Alternative Oilseed Milling Process", Journal of the American Oil Chemists' Society, 1974, vol. 51, pp. 137–141.

Cater, C. M. et al., "Cottonseed Protein Food Products", Journal of the American Oil Chemists' Society, 1977, vol. 54, pp. 90A–93A.

Davies, Peter L. et al., "Biochemistry of fish antifreeze proteins", The FASEB Journal, 1990, vol. 4, pp. 2460–2468.

Holbrook, Larry A. et al., "Oilbody Proteins in Microspore–Derived Embryos of *Brassica napus*$_1$", Plant Physiol., 1991, vol. 97, pp. 1051–1058.

Huang, Anthony H.C., "Oil Bodies and Oleosins in Seeds", Annu. Rv. Plant Physiol. Plant Mol. Biol., 1992, vol. 43, pp. 177–200.

Jacks, T. J. et al., "Isolation and Physicochemical Characterization of the Half–Unit Membranes of Oilseed Lipid Bodies", JAOCS, Jun. 1990, vol. 67, No. 6, pp. 353–361.

Knauf, V. C., "Genetic Bases of the biosynthesis of fatty acids: Designing the oils and fats of the future", Fat. Sci. Technol, 1994, vol. 96, No. 11, p. 408.

Kumar, N. S. K. et al., "A fresh look at coconut and its processing", INFORM, Nov. 1995, vol. 6, No. 11, pp. 1217–1240.

Lawhon, J. T. et al., "Evaluation of the Food Use Potential of Sixteen Varieties of Cottonseed", Journal of the American Oil Chemists' Society, 1977, vol. 54, pp. 75–80.

Leber, Regina et al., "Characterization of Lipid Particles of the Yeast, *Saccharomyces cerevisiae*", Yeast, 1994, vol. 10, pp. 1421–1428.

(List continued on next page.)

*Primary Examiner*—Thurman K. Page
*Assistant Examiner*—Marina Lamm
(74) *Attorney, Agent, or Firm*—Bereskin & Parr Micheline Gravelle

(57) ABSTRACT

The present invention provides novel adjuvants which comprise oil bodies. The invention also provides vaccine formulations comprising oil bodies and an antigen and methods for preparing the vaccines and the use of the vaccines to elicit an immune response.

13 Claims, 10 Drawing Sheets

OTHER PUBLICATIONS

Millichip, Mark et al., Purification and characterization of oil–bodies (oleosomes) and oil–body boundary proteins (oleosins) from the developing cotyledons of sunflower (*Helianthus annuus* L.), Biochem. J., 1996, vol. 314, pp. 333–337.

Monsalve, R. I. et al., "Detection, isolation and complete amino acid sequence of an aeroallergenic protein from rapeseed flour", Clinical and Experimental Allergy, 1997, vol. 27, pp.833–841.

Monsalve, R. I. et al., "Detection, isolation and complete amino acid sequence of an aeroallergenic protein from rapeseed flour", Clinical and Experimental Allergy, 1997, vol. 27, pp. 833–841.

Murphy, Denis J. et al., "Seed Oil–Bodies: Isolation, Composition and Role of Oil–Body Apolipoproteins", Phytochemistry, 1989, vol. 28, No. 8, pp. 2063–2069.

Murphy, Denis J. et al., "Structure and function of oleosins in oil plants", INFORM, Aug. 1993, vol. 4, No. 8, pp. 922–932.

Ogawa, Tadashi et al., "Identification of the Soybean Allergenic Protein, *Gly m* Bd 30K, with the Soybean Seed 34–kDa Oil–body–associated Protein", Biosci. Biotech. Biochem., 1993, vol. 57, No. 6, pp. 1030–1033.

Pieper–Fürst, Ursula et al., "Purification and Characterization of a 14–Kilodalton Protein that is Bound to the Surface of Polyhydroxyalkanoic Acid Granules in *Rhodococcus ruber*", Journal of Bacteriology, Jul. 1994, vol. 176, pp. 4328–4337.

Ross, Joanne H. E. et al., Differential presence of oleosins in oleogenic seed and mesocarp tissues in olive (*Olea europaea*) and avocado (*Persea americana*), Plant Science, 1993, vol. 93, pp. 203–210.

Roessler, Paul G., "Effects of Silicon Deficiency on Lipid Composition and Metabolism in the Diatom *Cyclotella Cryptica*, "J. Phycol., 1988, vol. 24, pp. 394–400.

Ting, Julie T. L. et al., "Oleosin of Plant Seed Oil Bodies Is Correctly Targeted to the Lipid Bodies in Transformed Yeasts", The Journal of Biological Chemistry, 1997, vol. 272, No. 6, pp. 3699–3706.

* cited by examiner

Figure 3: Oil Body Structure
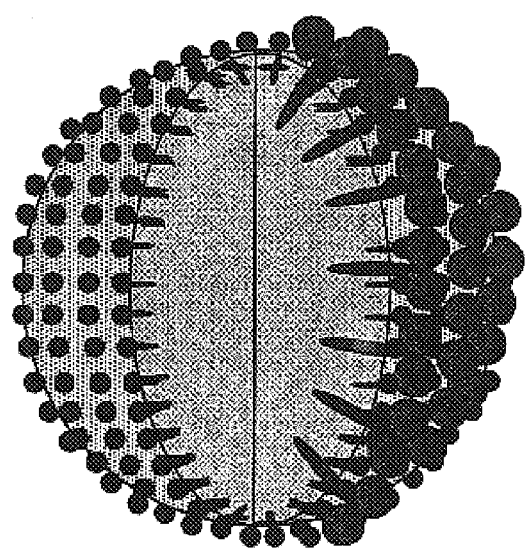
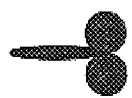 Oleosin
 Phospholipid
 Oil (Triglyceride)

Figure 4. Antigen Coupled to Oil-Body
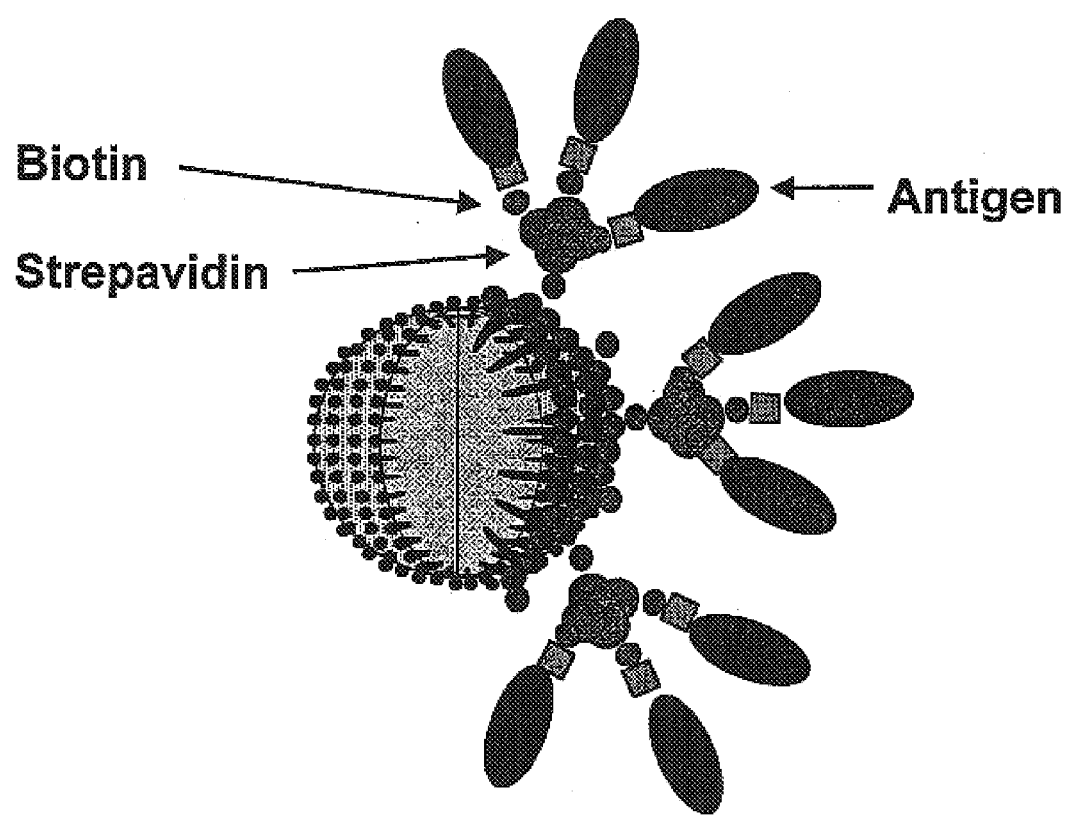

Figure 5: Transgenic Oil-Bodies Containing Antigen.
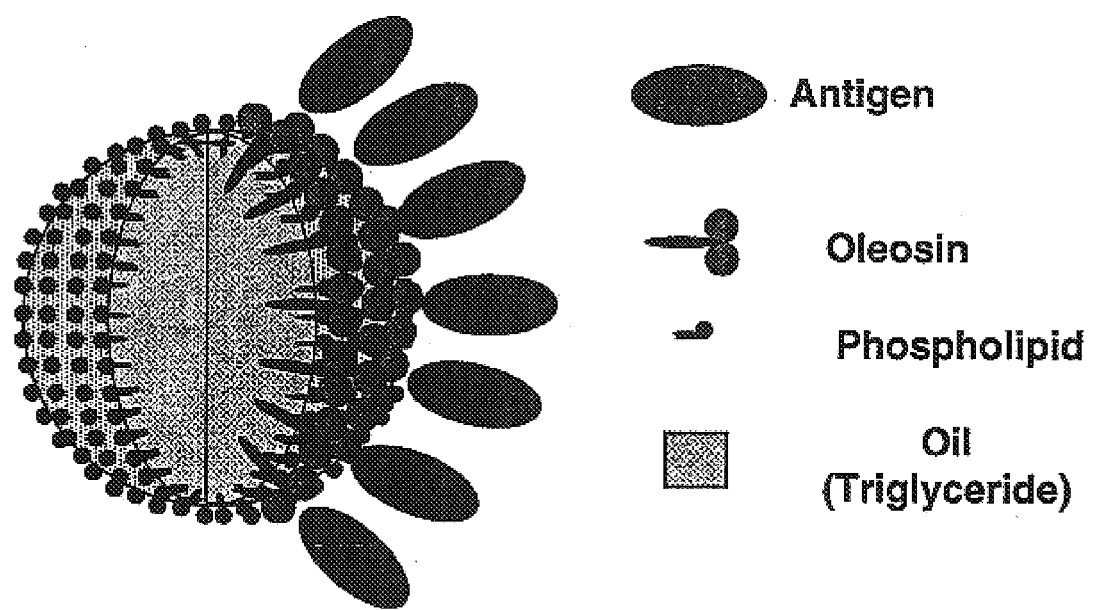

Figure 6: Comparison of Transgenic and Coupled Oil-Body for Antigen Presentation
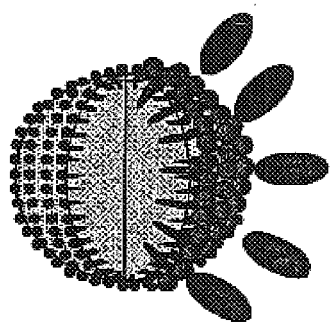 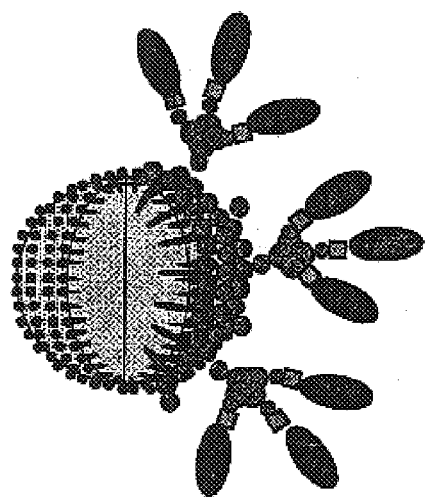
Transgenic Oil-body Antigen Presentation
Coupled Oil-body Antigen Presentation

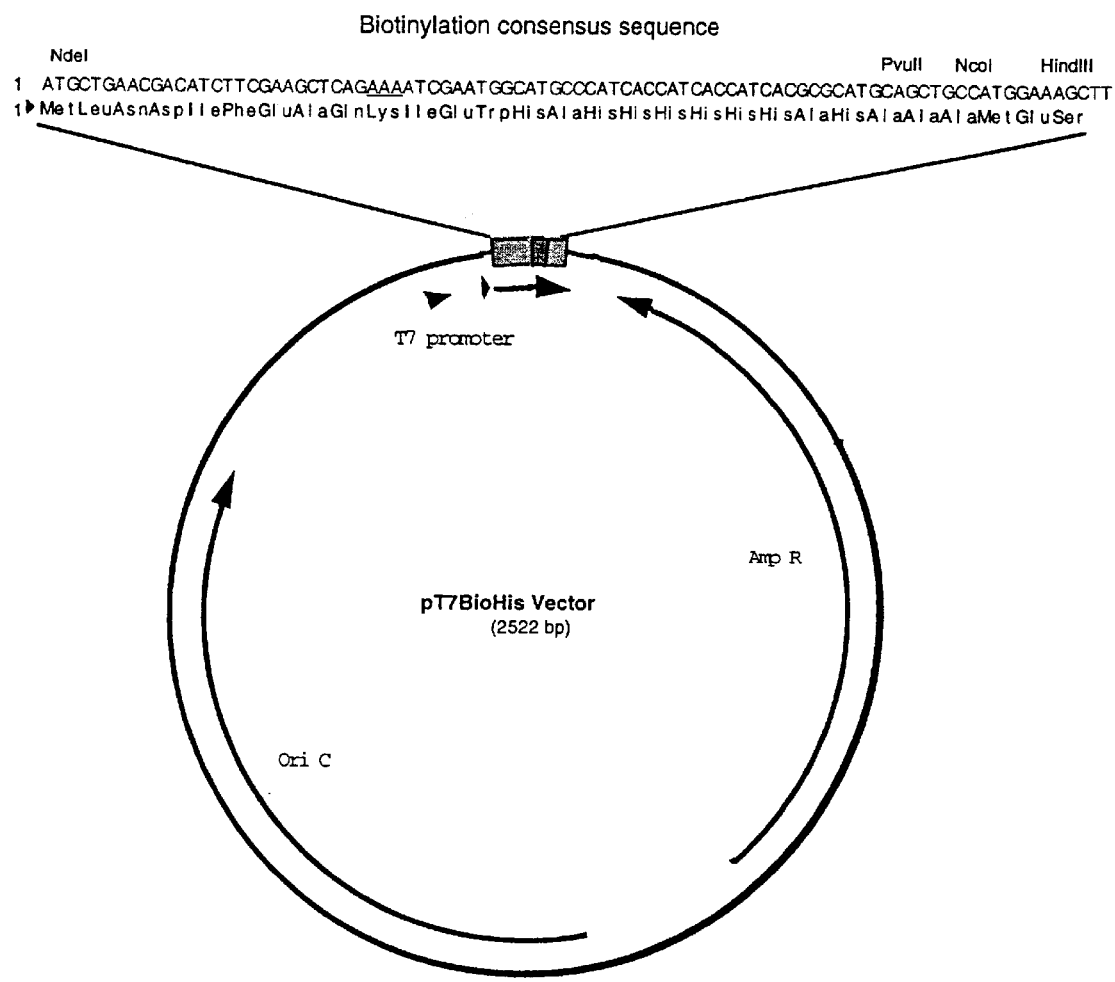
Figure 7. pT7BioHis Vector.

Figure 8: Plant Transformation Vector Encoding A Fusion Between Oleosin and the *Neisseria meningitidis* Transferrin Binding Protein B N-lobe.

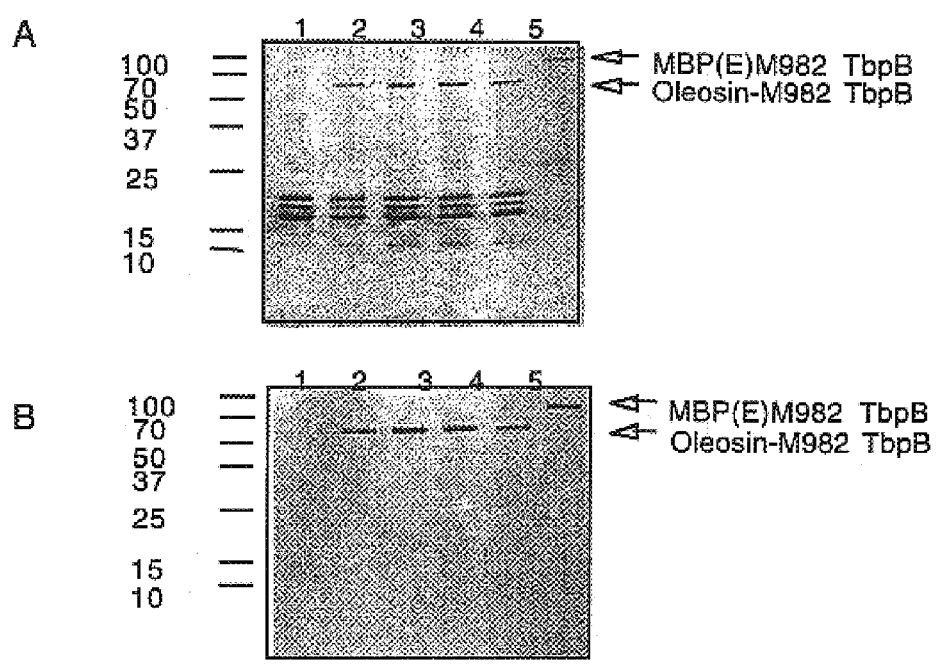
Figure 9. Analysis of *Arabidopsis* oil-bodies expressing oleosin-M982 TbpB N-lobe.

Figure 10. Transferrin binding analysis of transgenic *Arabidopsis* oilbodies expressing oleosin-M982 TbpB N-lobe.

SEQUENCE LISTING

<160> NUMBER OF SEQ ID NOS: 2

<210> SEQ ID NO 1
<211> LENGTH: 89
<212> TYPE: DNA
<213> ORGANISM: Artificial Sequence
<220> FEATURE:
<223> OTHER INFORMATION: Biotinylation consensus sequence
<221> NAME/KEY: CDS
<222> LOCATION: (1)..(87)
<223> OTHER INFORMATION:

<400> SEQUENCE: 1

```
atg ctg aac gac atc ttc gaa gct cag aaa atc gaa tgg cat gcc cat    48
Met Leu Asn Asp Ile Phe Glu Ala Gln Lys Ile Glu Trp His Ala His
1               5                   10                  15 cac cat cac cat cac gcg cat gca gct gcc atg gaa agc tt             89
His His His His His Ala His Ala Ala Ala Met Glu Ser
                20                  25
```

<210> SEQ ID NO 2
<211> LENGTH: 29
<212> TYPE: PRT
<213> ORGANISM: Artificial Sequence
<220> FEATURE:
<223> OTHER INFORMATION: Biotinylation consensus sequence

<400> SEQUENCE: 2

```
Met Leu Asn Asp Ile Phe Glu Ala Gln Lys Ile Glu Trp His Ala His
1               5                   10                  15

His His His His His Ala His Ala Ala Ala Met Glu Ser
                20                  25
```

IMMUNOGENIC FORMULATIONS COMPRISING OIL BODIES

This application is a continuation-in-part of U.S. patent application Ser. No. 09/577,147 filed May 24, 2000 now U.S. Pat. No. 6,372,234 which is a continuation-in-part of U.S. patent application Ser. No. 09/448,600 filed Nov. 24, 1999, now U.S. Pat. No. 6,183,762, which is a continuation-in-part of U.S. patent application Ser. No. 09/084,777 filed May 27, 1998, now U. Pat. No. 6,146,645, which claims benefit from U.S. provisional application No. 60/075,863, filed on Feb. 25, 1998 (now abandoned); U.S. provisional application No. 60/075,864 filed on Feb. 25, 1998 (now abandoned); U.S. provisional application No. 60/047,779, filed on May 28, 1997 (now abandoned); U.S. provisional application No. 60/047,753, filed May 27, 1997 (now abandoned). This application also claims benefit from U.S. provisional application No. 60/212,130, filed Jun. 16, 2000. All of the prior applications are incorporated herein by reference in their entirety.

FIELD OF THE INVENTION

The present invention provides novel adjuvants which comprise oil bodies and novel vaccines which comprise oil bodies and an antigen. The invention also provides a method for preparing the vaccines and the use of the vaccines.

BACKGROUND OF THE INVENTION

Emulsions are mixtures prepared from two mutually insoluble components. It is possible to generate mixtures of homogenous macroscopic appearance from these components through proper selection and manipulation of mixing conditions. The most common type of emulsions are those in which an aqueous component and a lipophilic component are employed and which in the art are frequently referred to as oil-in-water and water-in-oil emulsions. In oil-in-water emulsions the lipophilic phase is dispersed in the aqueous phase, while in water-in-oil emulsions the aqueous phase is dispersed in the lipophilic phase. Commonly known emulsion based formulations that are applied to the skin include cosmetic products such as creams, lotions, washes, cleansers, milks and the like as well as dermatological products comprising ingredients to treat skin conditions, diseases or abnormalities.

Generally emulsions are prepared in the presence of a multiplicity of other substances in order to achieve a desirable balance of emulsification, viscosity, stability and appearance. For example, the formulation of emulsions usually requires at least one, and frequently a combination of several, emulsifying agents. These agents facilitate the dispersal of one immiscible phase into the other and assist in stabilizing the emulsion. A comprehensive overview of emulsifying agents and their applications may be found in Becher, P. Encyclopedia of Emulsion Technology, Dekker Ed., 1983. Active agents beneficial to the skin, such as compounds to treat skin diseases, are also frequently formulated as emulsions in order to enhance their stability and to facilitate application of the active agent to the skin.

In the seeds of oilseed crops, which include economically important crops, such as soybean, rapeseed, sunflower and palm, the water insoluble oil fraction is stored in discrete subcellular structures variously known in the art as oil bodies, oleosomes, lipid bodies or spherosomes (Huang 1992, Ann. Rev. Plant Mol. Biol. 43: 177–200). Besides a mixture of oils (triacylglycerides), which chemically are defined as glycerol esters of fatty acids, oil bodies comprise phospholipids and a number of associated proteins, collectively termed oil body proteins. From a structural point of view, oil bodies are considered to be a triacylglyceride matrix encapsulated by a monolayer of phospholipids in which oil body proteins are embedded (Huang, 1992, Ann. Rev. Plant Mol. Biol. 43: 177–200). The seed oil present in the oil body fraction of plant species is a mixture of various triacylglycerides, of which the exact composition depends on the plant species from which the oil is derived. It has become possible through a combination of classical breeding and genetic engineering techniques, to manipulate the oil profile of seeds and expand on the naturally available repertoire of plant oil compositions. For an overview of the ongoing efforts in his area, see Designer Oil Crops/Breeding, Processing and Biotechnology, D. J. Murphy Ed., 1994, VCH Verlagsgesellschaft, Weinheim, Germany.

Plant seed oils are used in a variety of industrial applications, including the personal care industry. In order to obtain the plant oils used in these applications, seeds are crushed or pressed and subsequently refined using processes such as organic extraction, degumming, neutralization, bleaching and filtering. Aqueous extraction of plant oil seeds has also been documented (for example, Embong and Jelen, 1977, Can. Inst. Food Sci. Technol. J. 10: 239–243). Since the objective of the processes taught by the prior art is to obtain pure oil, oil bodies in the course of these production processes lose their structural integrity. Thus, the prior art emulsions formulated from plant oils generally do not comprise intact oil bodies.

Although fossil oil based products dominate certain markets, in other applications, oils derived from plant sources and fossil sources are in direct competition. Lauric oils, for example, which are widely used in the manufacture of detergents, are obtained from fossil oils as well as from coconut oil and more recently from genetically engineered rapeseed (Knauf, V. C., 1994, Fat. Sci. Techn. 96: 408). However, there is currently an increasing demand for biodegradable sources of raw materials. The plant oil body based emulsions of the present invention offer an advantage over similar mineral oil based formulations, in that the oil fraction is derived from a renewable and environmentally friendly source.

U.S. Pat. No. 5,683,740 to Voultoury et al. and U.S. Pat. No. 5,613,583 to Voultoury et al. disclose emulsions comprising lipid vesicles that have been prepared from crushed oleagenous plant seeds. In the course of the crushing process, oil bodies substantially lose their structural integrity. Accordingly, these patents disclose that in the crushing process, 70% to 90% of the seed oil is released in the form of free oil. Thus the emulsions which are the subject matter of these patents are prepared from crushed seeds from which a substantial amount of free oil has been released while the structural integrity of the oil bodies is substantially lost. In addition, the emulsions disclosed in both of these patents are prepared from relatively crude seed extracts and comprise numerous endogenous seed components including glycosylated and non-glycosylated non-oil body seed proteins. It is a disadvantage of the emulsions to which these patents relate that they comprise contaminating seed components imparting a variety of undesirable properties, which may include allergenicity and undesirable odour, flavour, colour and organoleptic characteristics, to the emulsions. Due to the presence of seed contaminants, the emulsions disclosed in these patents have limited applications.

There have been extensive efforts directed towards development of subunit vaccines for human and veterinary disease control over the past two decades. Subunit vaccines are based on individual components derived from an infective agent that trigger the immune response. Identification of an appropriate antigen is only a first step in the development of a subunit vaccine as an effective adjuvant and delivery system as well as an economical means of production and purification of the desired antigen is required.

An adjuvant is any material that can increase the specific humoral and/or cellular response(s) to antigens. This rather broad definition has resulted in a highly heterogeneous collection of compounds being recognized as adjuvants. Thus it has been difficult to define a precise mode of action that is common to all adjuvants. It is widely believed that many adjuvants (i.e. emulsions, alum) act by forming antigenic deposits at the site of inoculation which slowly release antigens to cells of the immune system. The slow release of antigen results in a prolonged stimulation of the immune system for protracted periods. The particulate nature of the deposit may also enhance the uptake of antigen by the antigen processing cells, an important step for fully stimulating the immune system. In addition, some adjuvants contain components that stimulate the cells of the immune system and thus enhance the response to the antigen included in the formulation. More recently, molecular adjuvants are being developed that can stimulate specific cells or target antigens to specific cells and thus potentially have a more directed and predictable effect. Regardless of the exact mechanism, both cell-mediated and humoral immunity may be stimulated to varying degrees depending upon the antigen, the adjuvant, the protocol and the species involved.

The classic example of a highly effective adjuvant for eliciting a persistent immunological response after injection was described by J. Freund, (J. Immunol. 60:383–98, 1948). Freunds complete adjuvant is a combination of a mineral oil emulsion and killed mycobacteria. Although Freunds adjuvant, and Freunds incomplete adjuvant (minus the mycobacteria) have been used extensively for immunization of laboratory animals for the production of antisera or immunological reagents, neither are acceptable for human clinical use because of side effects such as necrosis at the injection site. Other adjuvants that achieve a prolonged response are protein adsorbents such as aluminum hydroxide or aluminum phosphate. These substances provide a slow release but do not contribute to immunogenicity of the antigen itself.

Many of the known adjuvants can be grouped into one of four categories: (i) oil-based adjuvants, (ii) mineral-based adjuvants, (iii) bacterial products, or (iv) saponins and immunostimulating complexes. Oil-based adjuvants are prepared as water-in-oil or oil-in-water emulsions, commonly using pharmaceutical grade mineral oils that are nonmetabolizable. Freunds incomplete adjuvant is an example. The mineral-based adjuvants include aluminum hydroxide, aluminum phosphate and calcium phosphate. The ability of bacterial extracts to stimulate the immune system has been known for some time (i.e. mycobacterial extract in Freunds adjuvant). Several of the components that were responsible for immunostimulatory effects in bacterial extracts have been identified (i.e. muramyl dipeptide) and derivatives of these compounds have been developed in an attempt to reduce the undesired side effects when using these compounds. QuilA is an example of a saponin isolated from plants that has powerful immunostimulatory properties but can have adverse effects at higher doses. It has been included in a specifically formulated preparation of cholate and phospholipid to form what has been termed immunostimulating complexes (ISCOMs).

With the exception of ISCOMs, most of the conventional adjuvants are only useful for parenteral immunizations and alternative strategies had to been considered for enhancing mucosal immunizations. ISCOMs, biodegradable microspheres and liposomes are some examples of systems that have been developed and tested for mucosal immunization.

In order to develop a commercially viable and effective vaccine, the mass production of the selected antigenic substance and adjuvant delivery system must be cost effective. This situation is compounded by the fact that often more that one representative antigen (or more than one variant of an antigen) is required to provide adequate protection against the infective agent. Additionally, with an increasing number of specific vaccines being developed against different agents, there is a need for immunization with multiple antigens. This raises issues regarding compatibility of different antigens and vaccine formulations and significantly adds to the costs of developing vaccines. The potential for an increasing number of injections required for comprehensive immunization programs for children raises the additional concern that there may be reduced willingness to complete the entire series of injections which in turn reduces efficacy of immunization programs.

Thus it evident that alternative routes of administration that are more palatable to the vaccinee, particularly transdermal applications, would be ideal as a priming immunization, a booster immunization or perhaps as a complete replacement for parenteral immunizations.

SUMMARY OF THE INVENTION

The present invention relates to novel emulsion formulations which are prepared from oil bodies. The emulsion formulations of the subject invention are obtainable in non-toxic and pharmaceutically acceptable forms. The present inventors have found that the oil body fraction of living cells is useful in the formulation of several products including vaccines. Broadly stated, the present invention provides an emulsion formulation comprising washed oil bodies derived from a cell.

The present inventors have determined that oil bodies can be used as an adjuvant in a vaccine. Accordingly, the present invention provides an adjuvant comprising oil bodies. The invention further provides a vaccine formulation comprising oil bodies and an antigen.

The invention also provides methods for preparing the vaccine formulations and the use of the vaccines for eliciting an immune response.

Accordingly, the present invention provides a method for preparing emulsion formulations comprising: 1) obtaining oil bodies from a cell; 2) washing the oil bodies; and 3) formulating the washed oil bodies into an emulsion for use as an adjuvant in a vaccine formulation.

In a preferred embodiment of the invention, the washed oil body preparation is obtained from plant seeds, including seeds obtainable from flax, safflower, rapeseed, soybean, maize and sunflower. Accordingly, the invention provides a method for preparing the emulsion formulations from plant seeds comprising:

(a) grinding plant seeds to obtain ground seeds comprising substantially intact oil bodies;
(b) removing solids from the ground seeds;
(c) separating the oil body phase from the aqueous phase;
(d) washing the oil body phase to yield a washed oil body preparation; and
(e) formulating the washed oil body preparation into an emulsion for use as an adjuvant in a vaccine.

In an embodiment of the invention, a liquid phase is added to the seeds prior to or while grinding the seeds.

In a further preferred embodiment of the invention, formulating the emulsion further comprises adding an antigen to the washed oil body preparation to prepare a vaccine. The formulating can also include stabilizing the washed oil body preparation to prevent degradation of the oil bodies either by physical forces or chemical forces.

In another embodiment, the antigen can be physically associated with the oil bodies in the vaccine formulation either through covalent or non-covalent interactions. In a specific embodiment, the antigen can be prepared as a recombinant fusion protein with an oil body protein which targets the expression of the antigen on the oil bodies.

The vaccines of the present invention can be used to elicit an immune response against any antigen using any route of administration including transdermal or through the mucosa.

Additional advantages and features of the present invention will become apparent after consideration of the accompanying drawings and the following detailed description of the invention.

BRIEF DESCRIPTION OF THE DRAWINGS

FIG. 3 is a pictorial representation of a plant oil-body. The oil-body contains a central core of triglyceride with a surface layer consisting of a phospholipid monolayer and a protein 'coat' consisting predominantly of oleosin. The model is not drawn to scale as the phospholipid and oleosin are greatly exaggerated for illustrative purposes.

FIG. 4 is a pictorial representation of an antigen coupled to an oil-body by the use of biotin and streptavidin molecules. The antigen is biotinylated enzymatically at the N-terminus is coupled to a biotinylated preparation of oil-bodies with streptavidin as a bridging ligand. This schematic drawing is not drawn to scale. The proteins (antigen, streptavidin & oleosin), phospholipid and biotin are exaggerated in size for illustrative purposes.

FIG. 5 is a pictorial representation of a plant oil-body containing a recombinant oleosin protein with an antigenic determinant that is expressed on the surface of the oil-body. Specifically, FIG. 5 is a schematic representation of transgenic oil-bodies expressing a foreign antigen as a fusion with the oil-body protein, oleosin. Fusions of antigen to oleosin C- or N-termini are targeted to oil-bodies along with native oleosins. The fused antigen is thus expressed at the oil-body surface similar to antigens on bacterial or viral surfaces. The relative size of the oil-body is dramatically underrepresented in this figure.

FIG. 6 is a pictorial representation of two oil-body preparations, a oil-body derived from a transgenic plant containing a recombinant oleosin oil-body protein gene expressing an antigen on the oil-body surface and an antigen coupled to an oil-body by the use of strepavidin and biotin.

FIG. 7 is a plasmid map of the expression vector pT7BioHis. The essential features of the pT7BioHis vector are a T7 promoter for gene expression, the biotinylation consensus sequence shown in the green nucleotides where the epsilon amino group of the Lys residue (underlined) is biotinylated in *E. coli*, the blue nucleotides represent the 6XHis residues and the red nucleotides represent the multiple cloning site. Restriction sites are underlined for Ndel. Pvull, Ncol and Hindlll.

FIG. 8 is a plasmid map of the recombinant vector pSBS2004-92 M982 TbpB N-lobe. The essential features of pSBS2004-92 TbpB N-lobe are OriC and OripR1 for replication in *Escherichia coli* and *Agrobacterium tumefaciens*, respectively, and gentamycin resistance (GentR). The T-DNA segment that is get incorporated into the plant genome lies within the left and right borders and consists of the translation fusion between the Arabidopsis oleosin and M982 TbpB N-lobe driven is by the phaseolin promoter and its terminator and the herbicide selection marker, phosphinothricin (PptR).

FIG. 9 is a composite figure demonstrating the expression of *Neisseria meningitidis* TbpB N-lobe as an oleosin fusion protein in electroblots stained for protein (A) or detected with anti-oleosin antibody (B). Oil-bodies from several clones of transgenic Arabidopsis plants expressing the *N. meningitidis* strain M982 transferrin binding protein B (TbpB) N-lobe as a fusion with oleosin were analyzed for expression of fusion protein. Panel A shows a 15% SDS-PAGE gel stained for protein with Coomassie blue. Panel B shows a Western blot of the SDS-PAGE gel developed with polyclonal antibodies against M982 TbpB. Lane 1 shows oil-bodies from wild Arabidopsis; lane 2 shows oil-bodies from N1 transgenic line; lane 3 shows oil-bodies from N2 transgenic line; lane 4 shows oil-bodies from N3 transgenic line; lane 5 shows oil-bodies from N4 line, and lane 6 shows purified MBP-N-lobe fusion protein isolated from *E. coli*.

FIG. 10 is an electroblot demonstrating that the fusion protein of oleosin and *Neisseria meningitidis* TbpB N-lobe retains binding activity for human transferrin. Oil-bodies from several clones of transgenic Arabidopsis plants expressing the *N. meningitidis* strain M982 transferrin binding protein B (TbpB) N-lobe as a fusion with oleosin were analyzed for binding of human transferrin. A duplicate SDS-PAGE gel described in FIG. 7 was electroblotted and subsequently probed with human transferrin conjugated to horse radish peroxidase. Lane 1 shows oil-bodies from wild Arabidopsis; lane 2 shows oil-bodies from N1 transgenic line; lane 3 shows oil-bodies from N2 transgenic line; lane 4 shows oil-bodies from N3 transgenic line; lane 5 shows oil-bodies from N4 line, and lane 6 shows purified MBP-N-lobe fusion protein isolated from *E. coli*.

DETAILED DESCRIPTION OF THE INVENTION

I. Oil Bodies as Adjuvants

Figure 1:
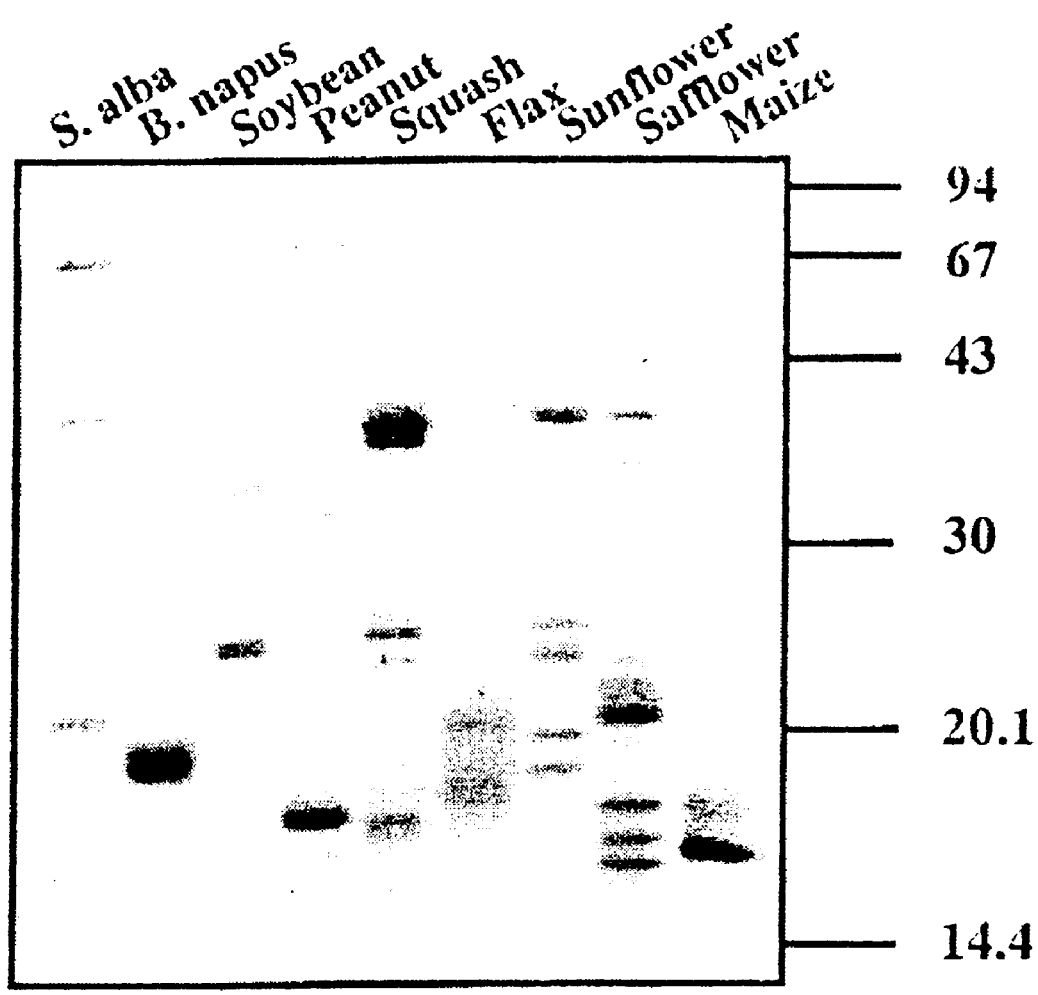
FIG. 1 is a Coomassie blue stained gel of a washed oil body preparation from white mustard, rapeseed (*Brassica napus*), soybean, peanut, squash, flax, sunflower, safflower and maize.

As hereinbefore mentioned, the present invention relates to emulsion formulations comprising oil bodies derived from a cell. The inventors have shown that oil bodies are useful as an adjuvant when used in a vaccine with an antigen. The oil bodies offer a safe and effective alternative to common adjuvants and they can be produced inexpensively on a large scale. Accordingly, in one embodiment, the present invention provides an emulsion formulation comprising washed oil bodies that are useful as an adjuvant in a vaccine. In a preferred embodiment, the washed oil bodies comprise substantially intact oil bodies.

In another embodiment, the present invention provides a method for preparing an emulsion formulation for use as an adjuvant comprising: 1) obtaining oil bodies from a cell; 2) washing the oil bodies; and 3) formulating the washed oil bodies into an emulsion for use as an adjuvant. Preferably, the washed oil bodies comprise substantially intact oil bodies.

In a preferred embodiment of the invention, formulating the washed oil bodies further comprises adding an antigen to the washed oil bodies.

The cell can be any cell that contains oil bodies (or oil body-like structures) including plant cells, animal cells, fungal cells and bacterial cells. In a preferred embodiment of the invention the oil bodies are obtained from a plant cell. The oil bodies may be obtained from a plant cell by rupturing the plant cell membrane and cell wall using any method which releases the cells constituents without substantially compromising the structural integrity of the oil bodies.

More preferably, the oil bodies are obtained from plant seeds. Accordingly, the present invention further provides a method for preparing an emulsion formulation comprising:
(1) obtaining oil bodies from plant seeds by a method that comprises:
   (a) grinding plant seeds to obtain ground seeds comprising substantially intact oil bodies;
   (b) removing solids from the ground seeds; and
   (c) separating the oil body phase from the aqueous phase;
(2) washing the oil body phase to yield a washed oil body preparation; and
(3) formulating the washed oil body preparation into an emulsion for use as an adjuvant in a vaccine formulation.

In a preferred embodiment of the invention, a liquid phase is added to the seeds prior to or while grinding the seeds.

The term "grinding" as used herein means milling, crushing, chopping or granulating the seeds and these terms may be used interchangeably throughout this application. In the process, the seed cells are broken open while the oil bodies remain substantially intact. The term "substantially intact" as used herein means that the oil bodies have not released greater than 50% (v/v) of their total seed oil content in the form of free oil. Preferably, grinding of the seeds results in release of less than about 50% (v/v) of the total seed oil content in the form of free oil, more preferably less than about 20% (v/v) and most preferably less than about 10% (v/v).

The term "solids" as used herein means any material that is not soluble in the aqueous phase or in the oil body phase, such as seed hulls.

The term "washing the oil bodies" as used herein means any process that removes cellular contaminants from the oil body phase, in particular any contaminant which imparts undesirable properties to the emulsion formulation, such as allergenic properties, undesirable color, odor, flavor or dermatological characteristics or any other undesirable property. Examples of methods of washing include gravitation based separation methods such as centrifugation and size exclusion based separation techniques such as membrane ultrafiltration and crossflow microfiltration. Washing methods and conditions are selected in accordance with the desired purity of the oil body preparation.

The term "washed oil body preparation" as used herein means a preparation of oil bodies from which a significant amount of cellular material has been removed including contaminants which impart undesirable properties to the emulsion formulation, such as allergenic properties, undesirable color, odor, taste or organoleptic characteristics or any other undesirable property. Preferably, the washed oil body preparation contains less than about 75% (w/w) of all endogenously present non-oil body seed proteins, more preferably the washed oil body preparation contains less than about 50% (w/w) of endogenously present non-oil body seed proteins and most preferably less than about 10%(w/w) of endogenously present non-oil body seed proteins.

By "formulating the oil bodies into an emulsion for use as an adjuvant in a vaccine formulation", it is meant that the washed oil body preparation is mixed, homogenized or prepared until an emulsion is formed that is suitable for use in a vaccine and when used in vaccine results in the generation of an immune response that is greater than when compared to a vaccine without the oil bodies. In a preferred embodiment, an additional ingredient is added, such as a liquid phase, and the washed oil body preparation and the additional ingredient are mixed until a homogenous mixture is attained.

The washed oil body preparations are particularly suitable for the formulation of emulsions such as vaccines due to advantageous properties outlined below.

Properties of the Oil Bodies

The emulsion formulations of the present invention comprise substantially intact washed oil bodies of approximately uniform size, shape and density. When viewed under the electron microscope, oil bodies are found to be more or less spherically shaped structures (see: Example Murphy, D. J. and Cummins I., 1989, Phytochemistry, 28: 2063–2069; Jacks, T. J. et al., 1990, JAOCS, 67: 353–361). Typical sizes of oil bodies vary between 0.4 micrometer and 1.5 micrometer (Murphy, D. J. and Cummins I., 1989, Phytochemistry, 28: 2063–2069). When analyzed using a Malvern Size Analyzer, it was found that oil bodies in a washed oil body preparation isolated from rapeseed were symmetrically and unimodally distributed around 1 micrometer. Using a Malvern Size Analyzer a washed oil body preparation could be clearly distinguished from commercially obtainable oil-in-water emulsions including soymilk, mayonnaise (Kraft Real Mayonnaise) and two coconut milk preparations (Tosca, Aroy-D). The exact size and density of the oil bodies depends at least in part on the precise protein/phospholipid/triacylglyceride composition which is present. Preparing washed oil bodies according to the present invention does not result in a substantive alteration in the shape of the oil bodies in comparison with those present in whole seed when viewed under the electron microscope.

Upon breaking open a cell containing oil bodies, the oil body fraction may be rapidly and simply separated from aqueous solutions since in aqueous solutions the oil body fraction will float upon application of centrifugal force. In solutions, where the density of the oil body fraction is greater than that of the solvent, such as 95% ethanol, the oil bodies will sediment under the same conditions. The oil body fraction may also be separated from the aqueous fraction through size-exclusion based separation techniques, such as membrane filtration, which may be advantageous in that more uniformly sized oil bodies may be acquired.

The oil bodies present in the washed oil body preparations of the present invention are resistant to exposure to strong acids and bases, including prolonged exposure to acidic conditions at least as low as pH 2 and alkaline conditions at least as high as pH 10. When exposed to pH 12, a slight loss of oil was observed, indicating a loss of integrity of the oil body structure. In addition, extraction with various organic solutions, including methanol, ethanol, hexane, isopropyl alcohol and ethyl acetate, does not or only slightly compromise the integrity of the oil bodies present in the washed oil body preparation. The oil bodies present in the washed oil body preparation were also found to withstand mixing with the anionic detergent, sodium dodecyl sulfate (SDS), the cationic, detergent hexadecyl trimethyl bromide and Tween-80, a non-ionic detergent. Boiling of the washed oil body preparation in the presence of SDS was found to result at least partly in disintegration of the oil body structure. The oil bodies present in the washed oil body preparation are stable when maintained for 2 hours up to at least 100° C. A slow freeze and thaw of washed oil body preparations resulted in a change in their physical appearance characterized by the formation of clumps as opposed to a homogeneous emulsion. Oil body clumping following a freeze-thaw could also be prevented to a large degree by either a) flash freezing in liquid nitrogen instead of slow freezing at −20° C. or b) adding glycerol in excess of 5% (v/v) to the oil body preparation prior to freezing. The resistance to relatively harsh chemical and physical conditions, is a unique characteristic of the oil bodies present in the washed oil body preparation of the subject invention.

The present invention provides emulsion formulations comprising oil bodies from which a significant amount of seed contaminants have been removed. These contaminants include proteins, volatiles and other compounds which may impart undesirable color, odor, flavor, organoleptic characteristics or other undesirable characteristics. A number of seed proteins have been reported to cause allergenic reactions. For example, Ogawa et al. (1993, Biosci. Biotechnol. Biochem., 57:1030–1033) report allergenicity of the soybean glycoprotein P34 (alternatively referred to as Gly m Bd 30K). Allergenic reactions against rapeseed, wheat and barley seed proteins have also been reported (Armentia et al., 1993., Clin. Exp. Allergy 23: 410–415; Monsalve et al., 1993, Clin. Exp. Allergy 27: 833–841). Hence removal of contaminating seed proteins is advantageous especially when used in vaccine formulations. Washing conditions may be selected such that a substantially pure oil body preparation is obtained. In that case, only the oil body proteins are substantially present in the preparation.

For many applications, it is also considered desirable that a purer better defined oil body preparation is obtained, as this allows more control over the formulation process of the final emulsion. In order for the washed oil body preparation to be included in a diverse set of emulsions it is desirable that volatiles are kept to a minimum and the color is preferably light or white. Washing of the oil body preparation results in a lighter colored preparation. In addition, a substantial amount of volatiles is removed. Also removed by washing are compounds which promote the growth of microorganisms as it was observed that a washed oil body preparation had a longer shelf life than an unwashed preparation. Other compounds which are removed by washing include anti-nutritional glucosinilates and/or breakdown products thereof and fibrous material. When heat treated to 60° C. or 80° C., it was observed that larger quantities of water remained absorbed by the washed oil body preparation when compared with an unwashed preparation. Upon cooling down to room temperature and centrifugation, it was observed that the washed oil body preparation remained stable, while phase separation occurred in the unwashed preparation. Given the enhanced stability of washed oil bodies, they are preferred where the formulation process involves the application of heat. When heated to 40° C., the washed oil body preparation was able to absorb a larger quantity of exogenously added water without resulting in phase separation. Thus in the formulation of aqueous emulsions, washed oil bodies are preferred. The capacity to absorb exogenously added oils was also compared between a preparation of washed oil bodies and an unwashed preparation. Larger amounts of exogenous oil could be added to the washed oil body preparation before an unstable emulsion was formed. This is advantageous in formulations where exogenous oils or waxes are added in the formulation process such as where personal care products are prepared. When viscosity was compared between a washed oil body preparation and an unwashed preparation it was found that the washed preparation was more viscous. A more viscous preparation of oil bodies is desirable as this allows for more flexibility in the formulation process and eliminates the need for the addition of thickening agents in the formulation process.

Thus the washed oil body preparation provided here is superior to an unwashed preparation in many respects. The washed oil body preparation of the present invention is a better defined preparation with a longer shelf life and more preferable color, odor and viscosity characteristics. The washed oil body preparation also has superior water and oil absorption characteristics. Finally due to the removal of a significant amount of seed proteins, allergenic reactions are less likely to occur. These characteristics allow the use of the washed oil body preparation in the formulation of a vaccine suitable for administration to humans and animals.

The above observations were made using washed and unwashed oil body preparations obtained from rapeseed and prepared as detailed in Example 2 of the present application. It is believed that resistance to relatively harsh chemical and physical conditions will be a characteristic of the oil bodies present in the washed oil preparation of the subject invention regardless of the source of the oil bodies. However one or more of the hereinbefore documented properties for rapeseed oil bodies may vary depending on the cells from which the washed oil bodies preparation is obtained. Nevertheless it is to be clearly understood that the subject invention is drawn to an oil body preparation which may be obtained from any cell comprising oil bodies.

In one embodiment of the present invention, the oil bodies are obtained from plant seeds. The presence of intact oil bodies in the emulsion and the described characteristics of these oil bodies clearly distinguish the subject emulsion formulation from other materials which may be prepared from plant seeds.

Sources and Preparation of the Oil Bodies

The washed oil body preparation of the subject may be obtained from any cell containing oil bodies or oil body-like organelles. This includes animal cells, plant cells, fungal cells, yeast cells (Leber, R. et al., 1994, Yeast 10: 1421–1428), bacterial cells (Pieper-Fürst et al., 1994, J. Bacteriol. 176: 4328–4337) and algae cells (Rossler, P. G., 1988, J. Physiol. (London) 24: 394–400).

In preferred embodiments of the invention the oil bodies are obtained from a plant cell which includes cells from pollens, spores, seed and vegetative plant organs in which oil bodies or oil body-like organelles are present (Huang, 1992, Ann. Rev. Plant Physiol. 43:177–200).

More preferably, the washed oil body preparation of the subject invention is prepared from plant seeds. Among the plant seeds useful herein preferred are those seeds obtainable from plant species selected from the group of plant species consisting of Brazil nut (*Bertholletia excelsa*); castor (*Ricinus communis*); coconut (*Cocus nucifera*); coriander (*Coriandrum sativum*); cottonseed (Gossypium spp.); groundnut (*Arachis hypogaea*); jojoba (*Simmondsia chinensis*); linseed/flax (*Linum usitatissimum*); maize (*Zea mays*); mustard (Brassica spp. and *Sinapis alba*); oil palm (*Elaeis guineeis*); olive (*Olea europaea*); rapeseed (Brassica spp.); safflower (*Carthamus tinctorius*); soybean (*Glycine max*); squash (*Cucurbita maxima*); sunflower (*Helianthus annuus*); and mixtures thereof.

Most preferred for use herein are oil bodies prepared from safflower (*Carthamus tinctorius*).

Plants are grown and allowed to set seed using agricultural cultivation practises well known to a person skilled in the art. After harvesting the seed and if desired removal of material such as stones or seed hulls (dehulling), by for example sieving or rinsing, and optionally drying of the seed, the seeds are subsequently processed by mechanical pressing, grinding or crushing. In a preferred embodiment, a liquid phase is added prior to or while grinding the seeds. This is known as wet milling. Preferably the liquid is water although organic solvents such as ethanol may also be used. Wet milling in oil extraction processes has been reported for seeds from a variety of plant species including: mustard (Aguilar et al 1990, Journal of Texture studies 22:59–84), soybean (U.S. Pat. No. 3,971,856; Carter et al., 1974, J. Am. Oil Chem. Soc. 51:137–141), peanut (U.S. Pat. No. 4,025,658; U.S. Pat. No. 4,362,759), cottonseed (Lawhon et al., 1977, J. Am. Oil, Chem. Soc. 63:533–534) and coconut (Kumar et al., 1995, INFORM 6 (11):1217–1240). It may also be advantageous to imbibe the seeds for a time period from about fifteen minutes to about two days in a liquid phase prior grinding. Imbibing may soften the cell walls and facilitate the grinding process. Imbibition for longer time periods may mimic the germination process and result in certain advantageous alterations in the composition of the seed constituents. Preferably the added liquid phase is water.

The seeds are preferably ground using a colloid mill, such as the MZ130 (Fryma Inc.). Besides colloid mills, other milling and grinding equipment capable of processing industrial scale quantities of seed may also be employed in the here described invention including: flaking rolls, disk mills, colloid mills, pin mills, orbital mills, IKA mills and industrial scale homogenizers. The selection of the mill may depend on the seed throughput requirements as well as on the source of the seed which is employed. It is of importance that seed oil bodies remain substantially intact during the grinding process. Grinding of the seeds therefore results in the release of preferably less than about 50% (v/v) of the total seed oil content in the form of free oil, more preferably less than about 20% (v/v) and most preferably less than about 10% (w/w). Any operating conditions commonly employed in oil seed processing, which tend to disrupt oil bodies are unsuitable for use in the process of the subject invention. Milling temperatures are preferably between 10° C. and 90° C. and more preferably between 26° C. and 30° C., while the pH is preferably maintained between 2.0 and 10.

Solid contaminants, such as seed hulls, fibrous material, undissolved carbohydrates and proteins and other insoluble contaminants, are removed from the crushed seed fraction. Separation of solid contaminants, may be accomplished using a decantation centrifuge, such as a HASCO 200 2-phase decantation centrifuge or a NX310B (Alpha Laval). Depending on the seed throughput requirements, the capacity of the decantation centrifuge may be varied by using other models of decantation centrifuges, such as 3-phase decanters. Operating conditions vary depending on the particular centrifuge which is employed and must be adjusted so that insoluble contaminating materials sediment and remain sedimented upon decantation. A partial separation of the oil body phase and liquid phase may be observed under these conditions.

Following the removal of insoluble contaminants, the oil body phase is separated from the aqueous phase. In a preferred embodiment of the invention a tubular bowl centrifuge is employed. In other embodiments, hydrocyclones, disc stack centrifuges, or settling of phases under natural gravitation or any other gravity based separation method may be employed. It is also possible to separate the oil body fraction from the aqueous phase employing size exclusion methods, such as membrane ultrafiltration and crossflow microfiltration. In preferred embodiments the tubular bowl centrifuge is a Sharples model AS16 (Alpha Laval) or a AS-46 Sharples (Alpha Laval). A critical parameter is the size of the ring dam used to operate the centrifuge. Ring dams are removable rings with a central circular opening varying, in the case of the AS-16, from 28 to 36 mm and regulate the separation of the aqueous phase from the oil body phase thus governing the purity of the oil body fraction which is obtained. In preferred embodiments, a ring dam size of 29 or 30 mm is employed when using the AS-16. The exact ring dam size employed depends on the type of oil seed which is used as well as on the desired final consistency of the oil body preparation. The efficiency of separation is further affected by the flow rate. Where the AS-16 is used flow rates are typically between 750–1000 ml/min (ring dam size 29) or between 400–600 ml/min (ring dam size 30) and temperatures are preferably maintained between 26° C. and 30° C. Depending on the model centrifuge used, flow rates and ring dam sizes must be adjusted so that an optimal separation of the oil body fraction from the aqueous phase is achieved. These adjustments will be readily apparent to a skilled artisan.

Separation of solids and separation of the aqueous phase from the oil body fraction may also be carried out concomitantly using a gravity based separation method such as 3-phase tubular bowl centrifuge or a decanter or a hydrocyclone or a size exclusion based separation method.

The compositions obtained at this stage in the process, generally are relatively crude and comprise numerous endogenous seed proteins, which includes glycosylated and non-glycosylated proteins and other contaminants such as starch or glucosinilates or breakdown products thereof. The present invention comprises the removal of a significant amount of seed contaminants. To accomplish removal of contaminating seed material, the oil body preparation obtained upon separation from the aqueous phase is washed at least once by resuspending the oil body fraction and centrifuging the resuspended fraction. This process yields what for the purpose of this application is referred to as a washed oil body preparation. The number of washes will generally depend on the desired purity of the oil body fraction. Depending on the washing conditions which are employed, an essentially pure oil body preparation may be obtained. In such a preparation the only proteins present would be oil body proteins. In order to wash the oil body fraction, tubular bowl centrifuges or other centrifuges such hydrocyclones or disc stack centrifuges may be used. Washing of oil bodies may be performed using water, buffer systems, for example, sodium chloride in concentrations between 0.01 M and at least 2 M, 0.1 M sodium carbonate at high pH (11–12), low salt buffer, such as 50 mM Tris-HCl pH 7.5, organic solvents, detergents or any other liquid phase. In preferred embodiments the washes are performed at high pH (11–12). The liquid phase used for washing as well as the washing conditions, such as the pH and temperature, may be varied depending on the type of seed which is used. Washing at a number of different pH's between pH 2 and pH 11–12 may be beneficial as this will allow the step-wise removal of contaminants, in particular proteins. Preferably washing conditions are selected such that the washed oil body preparation comprises less than about 75%(w/w) of all endogenously present non-oil body seed proteins, more preferably less than about 50% (w/w) of endogenously present non-oil body seed proteins and most preferably less than about 10% (w/w) of endogenously present non-oil body proteins. Washing conditions are selected such that the washing step results in the removal of a significant amount of contaminants without compromising the structural integrity of the oil bodies. In embodiments where more than one washing step is carried out, washing conditions may vary for different washing steps. SDS gel electrophoresis or other analytical techniques may conveniently be used to monitor the removal of endogenous seed proteins and other contaminants upon washing of the oil bodies. It is not necessary to remove all of the aqueous phase between washing steps and the final washed oil body preparation may be suspended in water, a buffer system, for example, 50 mM Tris-HCl pH 7.5, or any other liquid phase and if so desired the pH may be adjusted to any pH between pH 2 and pH 10.

The process to manufacture the washed oil body preparation may be performed in batch operations or in a continuous flow process. Particularly when tubular bowl centrifuges are used, a system of pumps operating between steps (a) and (b), (b) and (c), and (c) and (d) a continuous flow throughout the processing system is generated. In a preferred embodiment, the pumps are 1 inch M2 Wilden air operated double diaphragm pumps. In other embodiments, pumps, such as hydraulic or peristaltic pumps may be employed. In order to maintain a supply of homogenous consistency to the decantation centrifuge and to the tubular bowl centrifuge, homogenizers, such as an IKA homogenizer may be added between the separation steps. In-line homogenizers may also be added in between various centrifuges or size exclusion based separation equipment employed to wash the oil body preparations. Ring dam sizes, buffer compositions, temperature and pH may differ in each washing step from the ring dam size employed in the first separation step.

In embodiments of the invention where the oil bodies are isolated from softer tissues, for example the mesocarp tissue of olives, the techniques applied to break open the cell may vary somewhat from those used to break harder seeds. For example, pressure-based techniques may be preferred over crushing techniques. The methodology to isolate oil bodies on a small scale has been reported for isolation of oil bodies from mesocarp tissues in olive (*Olea europaea*) and avocado (*Persea americana*) (Ross et al., Plant Science, 1993, 93: 203–210) and from microspore-derived embryos of rapeseed (*Brassica napus*) (Holbrook et al., Plant Physiol., 1991, 97: 1051–1058).

In embodiments of the invention where oil bodies are obtained from non-plant cells, the washed oil body preparation is isolated following similar procedures as outlined above. The methodology for isolating oil bodies from yeast has been documented (Ting et al., 1997, Journal Biol. Chem. 272:3699–3706).

The chemical and physical properties of the oil fraction may be varied in at least two ways. Firstly, different plant species contain oil bodies with different oil compositions. For example, coconut is rich in lauric oils ($C_{12}$), while erucic acid oils ($C_{22}$) are abundantly present in some Brassica spp. Secondly, the relative amounts of oils may be modified within a particular plant species by applying breeding and genetic engineering techniques known to the skilled artisan. Both of these techniques aim at altering the relative activities of enzymes controlling the metabolic pathways involved in oil synthesis. Through the application of these techniques, seeds with a sophisticated set of different oils are obtainable. For example, breeding efforts have resulted in the development of a rapeseed with a low erucic acid content (Canola) (Bestor, T. H., 1994, Dev. Genet. 15: 458) and plant lines with oils with alterations in the position and number of double bonds, variation in fatty acid chain length and the introduction of desirable functional groups have been generated through genetic engineering (Töpfer et al., 1995, Science, 268: 681–685). Using similar approaches a person skilled in the art will be able to further expand on the presently available sources of oil bodies. Variant oil compositions will result in variant physical and chemical properties of the oil bodies. Thus by selecting oilseeds or mixtures thereof from different species or plant lines as a source for oil bodies, or by mixing oil bodies obtained from various species or plant lines, a broad repertoire of emulsions with different textures, different properties that are beneficial to the skin and different viscosities may be acquired.

Formulating the Emulsion

The washed oil body preparation may be formulated into an emulsion using techniques known in the art. Preferably, at least one additional ingredient is added to the washed oil body preparation. The additional ingredient may be any chemical compound, including without limitation any acid or base, any organic or inorganic molecule, any ionic or non-ionic compound, any polar or non-polar molecule and any lipophilic or hydrophilic compound or, if more than one additional ingredient is added, any mixture of these compounds. The additional ingredient may be added in any desirable form, for example, the additional ingredient may be added as a solution, suspension, a gel, a crystal, a liquid or solid and the additional ingredient may be of any desirable viscosity. Quantities of the additional ingredient may be as desired and will depend on the formulation. The additional ingredient may upon formulation become associated with the oil bodies for example by the formation of non-covalent or covalent chemical bonds with the oil body, remain suspended in solution, or form a suspension in which the oil bodies are dispersed. The additional ingredient may also penetrate the phospholipid monolayer surrounding the oil body or the triacylglyceride matrix. In a further preferred embodiment the liquid phase is water. Water may be added either directly or through moisture associated with another ingredient. The final amount of water is not critical, however generally, the compositions will contain at least 1% of water and up to 99% water.

The concentration of oil bodies in the final product may be as desired. Typically the final concentration of oil bodies varies from about 0.0000001% (w/v) to about 99.9999999% (w/v). Preferably the final concentration of oil bodies will vary from about 1% (w/v) to about 99% (w/v) and more preferably from about 2% (w/v) to about 60% (w/v). The final formulation may be a liquid or a solid and of any viscosity but in general the final formulation will be of a consistency and viscosity compatible with its use as a topically applied product.

In the course of the formulation process the oil bodies generally will stay intact, however depending on the ingredients that are added or the formulation process employed, the oil body structure may be more or less disrupted and the oil bodies may completely or partially disintegrate.

In the course of the formulation process any type of emulsion may be formed, including without limitation an oil-in-water emulsion, a water-in-oil emulsion, a multiple (e.g. double, tri-multiple, quarter-multiple and quinque-multiple etc.) emulsion, and reverse emulsion. The compositions of the present invention preferably will be in the form two phases where one phase is uniformly dispersed in the other phase, and resulting in a homogenous macroscopic appearance. Where compositions comprising two or more non-uniformly dispersed phases are formed they generally need to be shaken or stirred prior to application of the emulsion to the surface area of the body.

The final formulation may be of any pH, but is preferably of a pH compatible with application of the emulsion to a human such as to the skin mucosa or intraperitonealy. Usually the formulation process will require mixing to provide an adequate emulsion and it may be necessary to apply heat, pressure, freezing, one or more cycles of freeze thawing or other physical forces to formulate the emulsion.

II. Vaccine Formulations

The emulsion formulations for use as an adjuvant in a vaccine may be formulated in a wide range of vaccine formulations. Accordingly, the present invention provides a vaccine formulation comprising oil bodies and at least one antigen.

The present invention also includes the preparation of a vaccine formulation comprising oil bodies and an antigen. Accordingly, the present invention provides a method for preparing a vaccine formulation comprising:

(1) obtaining oil bodies from a cell;
(2) washing the oil bodies to obtain a washed oil body preparation; and
(3) adding an antigen to the washed oil body preparation and formulating into a vaccine.

In one embodiment, the present invention provides a method for preparing a vaccine formulation comprising:

(1) obtaining oil bodies from plant seeds by a method that comprises:
    (a) grinding plant seeds to obtain ground seeds comprising substantially intact oil bodies;
    (b) removing solids from the group seeds; and
    (c) separating the oil body phase from the aqueous phase;
(2) washing the oil body phase to yield a washed oil body preparation; and
(3) adding an antigen to the washed oil body preparation and formulating into a vaccine formulation.

A wide variety of antigens may be formulated with the washed oil bodies of the present invention. The amount of antigen formulated will depend on the desired effect and the antigen that is selected. In general, the amount of antigen (based on transgenic antigen/oleosin fusion) varies from about 0.0001% to about 50%. More preferably however the amount of antigen in the final composition will vary from about 0.01% to about 20% and most preferably from about 0.1% to about 10%. The antigens may be formulated into the washed oil body formulation in any desired manner (e.g. mixed, stirred) under any desired condition (e.g. heated; under pressure) and in any desired form (e.g. a liquid, solid, gel, crystal, suspension). Depending on the chemical nature of the active and the formulation methodology, the antigen may become incorporated in the final formulation in a variety of ways, for example the antigen may remain suspended in solution, or form a suspension in which the oil bodies are dispersed, or the antigen ingredients may penetrate the phospholid mono layer surrounding the oil body or the triacyl glyceride matrix of the oil body.

In a preferred embodiment, the antigen is associated with the oil bodies. As used herein the term "associated with the oil bodies" refers to any specific interaction between the antigen and the oil bodies including any interaction which involves the formation of a covalent bond between the oil body and the antigen as well as any interaction which involves the formation of a non-covalent bond, for example an ionic bond, between the oil body and the antigen. The antigen may directly associate with the oil body or indirectly via one or more intermediate molecules. As used herein "crosslinker" or "crosslinking agent" means any single molecule or plurality of inter-linked molecules capable of indirectly associating the active ingredient with the oil body. Oil bodies crosslinked to actives may comprise a plurality of covalent and non-covalent interactions or mixtures thereof. Generally the reaction to cross-link the antigen to the oil body will involve the oleosin protein or oil body phospholipids as reactive groups.

Particularly useful crosslinking agents for associating the antigen with the oil bodies are those crosslinking agents which are capable of reacting with oil body proteins. These include homobifunctional cross-linkers (i.e. having two identical reactive groups) including homobifunctional imido esters and homobifunctional N-hydroxysuccinimidyl (NHS) esters; and heterobifunctional crosslinkers (i.e. having two different reactive groups), including crosslinkers comprising an amine reactive group; sulffiydryl reactive N-hydroxysuccinimidyl esters such as maleimides pyridyl disulfides and alpha-haloacetyls; or a carboxyl reactive group. Non-limiting examples of crosslinking agents are inter alia dimethyladipimidate, discuccinidyl glutarate; succinimidyl 4-(N-maleimidomethyl) cyclo hexane-1-carboxylate, bismaleimidohexane; sulfosuccinimidyl (4-iodoacetyl)-aminobenzoate; N-succinimidyl 3-(2-pyridyldithione)-propionate; and 1-ethyl-3(3-dimethylaminopropyl)-carbodiimide; glutaraldehyde; and glyoxal.

Other useful crosslinkers include photoreactive crosslinkers such as arylazide derived compounds, for example p-azidophenyl glyoxal monohydrate; n-hydrosulfo-succinimidyl 4-azidobenzoate; and sulfosuccinimidyl (4-azidophenyldithio) propionate.

Still other components that are particularly useful as crosslinkers for the association of antigen to oil bodies are biotin-streptavidin and biotin-avidin crosslinkers (available from Pierce). By linking the antigen to streptavidin or avidin and biotinylating the oil bodies, or visa versa, biotinylating the antigen and linking avidin or streptavidin to the oil bodies, the antigen is crosslinked to the oil bodies via two inter-linked molecules. In a preferred embodiment, the oil bodies and antigen are biotinylated and are associated with each other by adding streptavidin. This embodiment is shown schematically in FIG. 4.

Accordingly, the present invention provides a method for preparing a vaccine formulation comprising oil bodies and an antigen, said method comprising:

(a) producing an antigen in a cell;
(b) associating said antigen with oil bodies through an oil body targeting protein capable of associating with said antigen and said oil bodies;
(c) obtaining the oil bodies associated with the antigen;
(d) washing the oil bodies to obtaining washed oil body preparation comprising the antigen; and
(e) formulating the washed oil bodies associated with the antigen into a vaccine formulation.

The term "oil body targeting protein" as used herein refers to any protein, protein fragment or peptide capable of associating with an oil body. In accordance with the present invention the oil body targeting protein that is used is also capable of associating with the antigen. The term "capable of associating with the antigen" as used herein refers to covalent interactions (i.e. protein fusions) as well as non-covalent interactions between the oil body targeting protein and the antigen. The oil body targeting protein that may be used in accordance with the present invention may be any oil body targeting protein, protein fragment or peptide capable of association with the antigen polypeptide and the oil bodies. The nucleic acid sequence encoding the oil body targeting peptide may be synthesized or obtained from any biological source.

Still further oil body targeting proteins which may be used in accordance with the present invention are one or more inter-linking antibodies. Particularly useful in this regard are antibodies with an affinity to oleosins. Combined inter-linked antibody-avidin-biotin or antibody-streptavidin-biotin cross-linkers may also be used in accordance with the present invention. In one embodiment the oil body targeting protein is an immunoglobulin or an immunoglobulin derived molecule, for example a bispecific single chain antibody. The generation of single chain antibodies and bi-specific single chain antibodies is known to the art (U.S. Pat. Nos. 5,763,733, 5,767,260 and 5,260,203). Nucleic acid sequences encoding single chain antibodies functioning as oil body targeting proteins may be prepared from hybridoma cell lines expressing monoclonal antibodies raised against an oleosin as described by Alting-Mees et al (2000) IBC's Annual International Conference on Antibody Engineering, Poster #1. In order to attain specificity for the antigen polypeptide a nucleic acid sequence encoding a second single chain antibody prepared from a monoclonal raised against the antigen polypeptide may be prepared and linked to the anti-oleosin single chain antibody. In this embodiment the oil body associates with the antigen polypeptide through non-covalent interactions of the oil body targeting protein with the antigen polypeptide and the oil body. Alternatively, the antigen polypeptide may be prepared as a fusion protein with an oil body targeting protein. For example a nucleic acid sequence encoding a single chain antibody raised against an oleosin may be fused to a nucleic acid sequence encoding antigen polypeptide Non-immunoglobulin-based oil body targeting proteins capable of association with an antigen polypeptide may be discovered and prepared using for example phage display techniques (Pharmacia Biotech Catalogue Number 27-9401-011 Recombinant Phage Antibody System Expression Kit).

Oil body targeting proteins may also be chemically modified. For example oleosins may be modified by changing chemical modification of the lysine residues using chemical agents such as biotinyl-N-hyrdoxysuccinimide ester resulting a process referred to as biotinylation. Conveniently this is accomplished by in vitro biotinylation of the oil bodies. In vivo biotinylation may be accomplished using the biotinylation domain peptide from the biotin carboxy carrier protein of E. coli acetyl-CoA carboxylase (Smith et al. (1998) Nucl. Acids. Res. 26: 1414–1420). Avidin or streptavidin may subsequently be used to accomplish association of the antigen with the oil body.

In a preferred embodiment the oil body targeting protein is an oil body protein such as for example an oleosin or a sufficient portion derived thereof capable of targeting to an oil body. Nucleic acid sequences encoding oleosins are known to the art. These include for example the Arabidopsis oleosin (Van Rooijen et al (1991) Plant Mol. Bio. 18:1177–1179); the maize oleosin (Qu and Huang (1990) J. Biol. Chem. Vol. 265 4:2238–2243); rapeseed oleosin (Lee and Huang (1991) Plant Physiol. 96:1395–1397); and the carrot oleosin (Hatzopoulos et al (1990) Plant Cell Vol. 2, 457–467.). In preferred embodiments of the invention the antigen polypeptide is fused to the oil body protein. The methodology is further described in U.S. Pat. No. 5,650,554, which is incorporated herein by reference in its entirety. In such an embodiment the oil bodies and the associated antigen polypeptide can conveniently be isolated in one step. The antigen polypeptide may be fused to the N-terminus as well as to the C-terminus of the oil body protein (as described in: van Rooijen and Moloney (1995) Plant Physiol. 109:1353–1361) and fragments of the oil body protein such as for example the central domain of an oleosin molecule, or modified versions of the oil body protein may be used. This embodiment is shown schematically in FIG. 5.

New oil body proteins may be discovered for example by preparing oil bodies (described in further detail below) and identifying proteins in these preparations using for example SDS gel electrophoresis. Polyclonal antibodies may be raised against these proteins and used to screen cDNA libraries in order to identify nucleic acid sequences encoding oil body proteins. The methodologies are familiar to the skilled artisan (Huynh et al. (1985) in DNA Cloning Vol. 1. a Practical Approach ed. DM Glover, IRL Press, pp 49–78). New oil body proteins may further be discovered using known nucleic acid sequences encoding oil body proteins (e.g. the Arabidopsis, rapeseed, carrot and corn nucleic acid sequences) to probe for example cDNA and genomic libraries for the presence of nucleic acid sequences encoding oil body proteins.

Accordingly, in a specific embodiment, the present invention provides a method for the preparation of a vaccine formulation comprising:

(a) introducing into a cell a chimeric nucleic acid sequence comprising:
1) a first nucleic acid sequence capable of regulating transcription in said cell operatively linked to;
2) a second nucleic acid sequence encoding a recombinant fusion polypeptide comprising (i) a first nucleic acid sequence encoding a sufficient portion of an oil body protein to provide targeting to an oil body linked in reading frame to (ii) a second nucleic acid sequence encoding an antigen operatively linked to;
3) a third nucleic acid sequence capable of terminating transcription in said cell;

(b) growing said cell under conditions to permit expression of said antigen in a progeny cell comprising oil bodies;

(c) isolating said oil bodies from comprising the antigen;

(d) washing said oil bodies to obtain a washed oil body preparation comprising the antigen; and (e) formulating said oil bodies comprising the antigen into a vaccine formulation.

One skilled in the art will appreciate that the antigen used in the vaccines of the invention can be any antigen to which one wishes to generate an immune response. The scope of the invention is not limited by the type of antigen used or the means by which the antigen is produced. Antigens may consist of peptides, proteins, carbohydrate or synthetically produced chemicals. The antigen may be similar or identical to the natural molecule against which an immune response is desired or may simply resemble the natural molecule sufficiently to be able to induce a response against the natural molecule. Due to the wide range of possibilities for production and use of antigens it is impossible to provide a comprehensive list of potential antigens that could be included in immunizations with oil bodies and thus only examples that may be reflective of the type of antigens that could be considered are provided.

The antigens may be derived from or represent molecules from infectious agents (bacteria, viruses, parasites) and may be used to generate in immune response to eliminate or reduce the effects of infection by the infectious agent. The antigen may be derived from or represent a component of a cancer cell and be used to generate an immune response to help eliminate the cancer cells. The antigen may be derived from or represent molecules that are involved directly or indirectly in an autoimmune response and may be use to modulate the immune response to reduce the undesired effects of the autoimmune disease.

Peptides and proteins antigens can be derived from or represent different types of proteins from pathogenic organisms and be used to induce an immune response that reduces or eliminates the pathogen or the effects that the pathogen has on the host. The various types of proteins can be classified on the basis of how they are produced or alternatively on the role that the protein plays in the interaction of the pathogen with the host.

One type of protein is secreted by a bacterial or parasitic pathogen and can be subclassified on the basis of its function or role. Secreted proteins include toxins secreted by bacterial or parasitic pathogens and includes secreted bacterial toxins such as diptheria toxin, pertussis toxin, dermnecrotic toxin, tetanus toxin, *E. coli* heat-labile toxin, cholera toxin, shiga toxin, Staphylococcus α toxin, toxic shock syndrometoxin among many others. Another example of secreted proteins that could serve as antigens include proteases such as elastase, metaloprotease, Iga protease (from *Haemophilus influenzae*, Neisseria spp. or *Streptococcus pneumoniae*) or hyaluronidase (from Streptococcus or Staphylococcus). Another example of secreted proteins that could serve a useful antigens include haemolysins or leukotoxins including streptolysin O or S, pneumolysin or leukotoxins from *Pasteurella haemolytica, Pasteurella multocida, Actinobacillus pleuropneumonia* or *Actinobacillus actinomycetencomitans*. Another example of secreted proteins are enzymes such as kinases including streptokinase and staphylokinase. Another example of secreted proteins are those that may be secreted into the eukaryotic host cell by means of the bacterial type III secretion system and include effector proteins from many Gram-negative bacterials species including Yersinia (invasin), Listeria (internalin) and Salmonella (subversin).

A second type of protein is a surface molecule of a pathogenic organism. As with secreted proteins, the surface proteins can be subclassified based on the function that the protein provides for pathogen. In Gram-negative bacteria, porin proteins that are involved in the movement of small molecules across the outer membrane are being evaluated as potential vaccine antigens against infections by Neisseria spp., Pseudomonas aeruginosa and *Escherichia coli* among many others. A second type of surface protein are surface receptors or binding proteins that are involved in transport functions or binding to host extracellular matrix proteins. These include the transferrin and lactoferrin receptor proteins from Neisseria spp., *Haemophilus influenzae, Moraxella catarrhalis, Pasteurella haemolytica, Actinobacillus pleuropneumoniae* and many other species, heme or haemoglobin binding proteins and siderophore receptors and fibrinogen-binding protein from Streptococcus. A third type of surface protein is an adhesin, which is involved in attachement to or adherence to the host cells directly or via extracellular host proteins. These include components of pili or fimbria from Neisseria, Haemophilus, Pseudomonas, *Escherichia coli,* Streptococcus and many other Gram-negative and Gram-positive bacteria. They also include surface adhesins such as intimin from *E. coli,* M proteins from Streptococcus species, the high molecular weight adhesins from non-typable *Haemophilus influenzae* and Usp proteins from *Moraxella catarrhalis.* Another type of surface antigen is one involved in motility such as flagellar proteins in Pseudomonas and Burkholderia species, members of the Enterobacteriacea and many other bacterial species. There are also many surface proteins for which the function is unknown which are being evaluated as potential vaccine antigens.

Another type of surface protein are the proteins found on the surface of an viral particle. This includes capside proteins such as the polio capsid proteins, group specific angigens, and envelope proteins such as Hepatitis B surface antigen, glycoproteins and hemagglutinins.

Carbohydrates are important surface molecules of pathogenic organisms and of host cells and are important antigens for infectious diseases and cancer. Antibody responses against carbohydrates can be accomplished by immunizing with carbohydrates mixed or conjugated with other molecules or my immunizing with proteins that mimic carbohydrate antigens.

Many pathogenic organisms have surface capsules consisting of carbohydrate polymers. Bacterial capsules from *Neisseria meningitidis, Streptococcus pneumoniae,* Streptococcus groups A and B and *Haemophilus influenzae* are examples of capsules used for vaccine production and development. Purified capsular carbohydrates were used for the first generation of capsular vaccines and improved versions of these vaccines are available (*Haemophilus influenzae*) or are being tested (*Neisseria meningitidis, Streptococcus pneumoniae*). Capsular vaccines are also being considered for fungal diseases such a histoplasmosis and crytococcus. Lipopolysaccharides and lipooligosaccharides are prominent surface components of all Gram-negative bacterial species and would be very usefull targets for the immune response were it not for the intrinsic toxicity of these molecules. Glycolipids are signficant components of the surface of mycobacteria (i.e. *Mycobacterium tuberculosis*) and mycoplasma and are potential vaccine antigens. Blood group antigens such as the Lewis blood group antigens (for breast cancer metastases) are important for vaccine consideration in cancer therapy.

One particularly preferred class of antigens which may be used in accordance with the present invention are proteins and peptides. Proteins and peptides are preferred as they may be prepared as a recombinant fusion protein with an oil body protein as hereinbefore described.

Protein or peptide antigens may also be administered in the vaccine formulation as a nucleic acid encoding the antigen. Such nucleic acids include free or naked RNA or DNA or in a vector. In a preferred embodiment, the nucleic acid sequence is contained in a vector or plasmid. In one embodiment, the vector may be viral such as poxvirus, adenovirus or alphavirus. Preferably the viral vector is incapable of integration in recipient animal cells. The elements for expression from said vector may include a promoter suitable for expression in recipient animal cells.

The following optional ingredients and mixtures thereof represent non-limiting examples of ingredients that may be additionally formulated with oil bodies and the antigen in order to prepare a vaccine formulation.

Carriers/Auxiliary Agents

The vaccines of the invention may be in admixture with a suitable carrier, diluent, or excipient such as sterile water, physiological saline, glucose or the like to form suitable vaccine formulations. The vaccines can also be lyophilized.

The vaccines may also contain auxiliary substances such as wetting or emulsifying agents, pH buffering agents, gelling or viscosity enhancing additives, preservatives, flavoring agents, colors, and the like, depending upon the route of administration and the preparation desired. In this regard, reference can be made to U.S. Pat. No. 5,843,456. Reference can also be made to the textbook Vaccine Design: the Subunit and Adjuvant Approach, Michael F. Powell and Mark J. Newman, eds. Plenum Press, New York, 1995.

Adjuvants

Although the oil bodies themselves act as an adjuvant in the vaccines of the invention, the vaccine may additionally include other adjuvants. A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

U.S. Pat. No. 4,855,283 granted to Lockhoff et al on Aug. 8, 1989, which is incorporated herein by reference thereto, teaches glycolipid analogues including N-glycosylamides, N-glycosylureas and N-glycosylcarbamates, each of which is substituted in the sugar residue by an amino acid, as immunomodulators or adjuvants. Thus, Lockhoff et al. (Chem. Int. Ed. Engl. 30:1611–1620 (1991)) reported that N-glycolipid analogs displaying structural similarities to the naturally-occurring glycolipids, such as glycophospholipids and glycoglycerolipids, are capable of eliciting strong immune responses in both herpes simplex virus vaccine and pseudorabies virus vaccine. Some glycolipids have been synthesized (from long chain-alkylamines and fatty acids that are linked directly with the sugars through the anomeric carbon atom) to mimic the functions of the naturally occurring lipid residues.

U.S. Pat. No. 4,258,029 granted to Moloney and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Nixon-George et al. (J. Immunol. 14:4798–4802 (1990)) have also reported that octadecyl esters of aromatic amino acids complexed with a recombinant hepatitis B surface antigen enhanced the host immune responses against hepatitis B virus. Adjuvant compounds may also be chosen from the polymers of acrylic or methacrylic acid and the copolymers of maleic anhydride and alkenyl derivative.

Adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, Jun. 1996). Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCl 9 g/l) all at once in several portions with concomitant or subsequent neutralization (pH 7.3 to 7.4), preferably with NaOH. This solution at physiological pH will be used as it is for mixing with the vaccine, which may be especially stored in freeze-dried, liquid or frozen form. The polymer concentration in the final vaccine composition will be 0.01% to 2% w/v, more particularly 0.06 to 1% w/v, preferably 0.1 to 0.6% w/v.

Persons skilled in the art can also refer to U.S. Pat. No. 2,909,462 (incorporated herein by reference) which describes such acrylic polymers cross-linked with a polyhydroxylated compound having at least 3 hydroxyl groups (preferably not more than 8), the hydrogen atoms of the at least three hydroxyls being replaced by unsaturated aliphatic radicals having at least 2 carbon atoms. The preferred radicals are those containing from 2 to 4 carbon atoms (e.g. vinyls, allyls and other ethylenically unsaturated groups). The unsaturated radicals may themselves contain other substituents, such as methyl. The products sold under the name Carbopol (BF Goodrich, Ohio, USA) are particularly appropriate. They are cross-linked with allyl sucrose or with allyl pentaerythritol. Among them, there may be mentioned Carbopol (for example, 974P, 934P and 971P). Among the copolymers of maleic anhydride and alkenyl derivative, the copolymers EMA (Monsanto; which are copolymers of maleic anhydride and ethylene, linear or cross-linked, (for example cross-linked with divinyl ether)) are preferred. Reference may be made to J. Fields et al. (Nature, 1960, 186: 778–780) for a further description of these chemicals (incorporated (herein by reference).

In one aspect of this invention, adjuvants useful in any of the embodiments of the invention described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the Clostridium difficile toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions of the invention include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium,* or *Shigella flexneri,* saponins, or polylactide glycolide (PLGA) microspheres) can also be used in mucosal administration.

Adjuvants useful for both mucosal and parenteral immunization include polyphosphazene (for example, WO 95/2415), DC-chol (3 b-(N-(N',N'-dimethyl aminomethane)-carbamoyl) cholesterol (for example, U.S. Pat. No. 5,283,185 and WO 96/14831) and QS-21 (for example, WO 88/9336).

Emulsion Stabilizing Agents

In a preferred embodiment of the present invention, the washed oil body preparation is stabilized so that an emulsion is obtained which may be stored for longer periods of time. For the purpose of the present application the term "stabilized oil body preparation" refers to an oil body emulsion that is prepared so that the oil body emulsion does not undergo undesirable physical or chemical alterations when the oil body emulsion is stored for long periods of time. Preferably the oil body preparation is prepared to be stable for at least 1 month, more preferably the preparation is stable for at least 1 year, and most preferably the preparation is stable at least 2 years when stored at room temperature. In a further preferred embodiment, the oil body emulsion is prepared so that the preparation additionally can withstand temperature fluctuations such as those which typically occur in non-temperature controlled environments for example during transport. In a stable oil body preparation alterations over time with respect to color, odor, viscosity, texture, pH and microbial growth are minimal or absent.

Generally, the emulsion formulations will be treated such that contamination by bacteria, fungi, mycoplasmas, viruses and the like or undesired chemical reactions, such as oxidative reactions are prevented. In preferred embodiments this is accomplished by the addition of preservatives, for example sodium metabisulfite; Glydant Plus; Phenonip; methylparaben; propylparaben; Germall 115; Germaben II; phytic acid; and mixtures thereof. The preparation may also be stabilized by irradiation, for example by ionizing radiation such as cobalt-60 or cesium-137 irradiation or by ultraviolet irradiation or by heat treatment for example by pasteurization in a constant temperature water bath at approximately 65° C. for 20 minutes. The pasteurization temperature preferably ranges between 50° C. and 90° C. and the time for pasteurization preferably ranges between 15 seconds to 35 minutes.

Oxidative reactions may be prevented by the addition of anti-oxidants such as for example butylated hydroxytoluene (BHT); butylated hydroxyanisol (BHA); ascorbic acid (vitamin C); tocopherol; phytic acid; citric acid; pro-vitamin A; and mixtures thereof.

The physical stability of the formulation may be further enhanced by the addition of for example an emulsifier such as an Arlacel such as Arlacel 165 or Glucamate LT or by the addition of viscosity modifiers such as such as cetyl alcohol; glycerol or Keltrol. The emulsion may be thickened and stabilized using gelling agents such as cellulose and derivatives; Carbopol and derivatives; carob; carregeenans and derivatives; xanthane gum; sclerane gum; long chain alkanolamides; bentone and derivatives; Kaolin USP; Veegum Ultra; Green Clay; Bentonite NFBC; and mixtures thereof. These agents are typically present in concentrations less than about 2% by weight.

The oil body preparation may also be further stabilized by modifying the pH and by modifying the ionic strength for example by adjusting the concentration of calcium or sodium ions. Examples of formulations of stabilized oil body preparations are shown in Example 6.

The following additional ingredients may be formulated with the stabilized oil body formulation. While in preferred embodiments of the present invention, the oil bodies are stabilized prior to the formulation with these additional ingredients, it is nevertheless possible to formulate the oil body preparation and stabilize the final formulation.

III. Uses of the Vaccine Formulations

The subject invention is directed toward the production of emulsions that are useful in a wide variety of applications including as an adjuvant in a vaccine formulation.

Accordingly, the present invention provides a method of eliciting an immune response comprising administering an effective amount of a vaccine formulation comprising oil bodies and an antigen to an animal in need thereof.

The term "eliciting an immune response" is defined as causing, enhancing, or improving any response of the immune system, for example, of either a humoral or cell-mediated nature. Whether a vaccine or antigen elicits an immune response can be assessed using assays known to those skilled in the art including, but not limited to, antibody assays (for example ELISA assays), antigen specific cytotoxicity assays and the production of cytokines (for example ELISPOT assays). Preferably, the method of the present invention enhances a cellular immune response, more preferably a cytotoxic T cell response.

The term "an effective amount" of the vaccine of the present invention is defined as an amount effective, at dosages and for periods of time necessary to achieve the desired result (e.g. elicit an immune response). The effective amount of a compound of the invention may vary according to factors such as the disease state, age, sex, and weight of the animal. Dosage regimes may be adjusted to provide the optimum therapeutic response. For example, several divided doses may be administered daily or the dose may be proportionally reduced as indicated by the exigencies of the therapeutic situation.

The term "antigen" as used herein refers to any molecule to which one wishes to elicit an immune response.

The term "vaccine" as used herein refers to any composition capable of eliciting an immune response.

The term "animal" as used herein includes all members of the animal kingdom, including humans. Preferably, the animal to be treated is a human.

The term "administering" is defined as any conventional route for administering an antigen to an animal for use in the vaccine field as is known to one skilled in the art. This may include, for example, administration via the topical, oral and parenteral (i.e. subcutaneous, intradermal, intramuscular, etc.) routes and further includes, transdermal and mucosal delivery, including mucosal delivery accomplished by oral feeding, inhaling and through the membranes accessible through the terminal portions of the large intestine.

A particularly preferred method of immunizing an animal with the vaccine encompasses a prime-boost protocol. Typically, a prime-boost protocol involves an initial administration of the vaccine followed by a boost of the vaccine. This protocol will elicit an enhanced immune response relative to the response observed following only one administration of the vaccine. An example of a prime-boost methodology/protocol is described in WO 98/58956, which is incorporated herein by reference. In the prime-boost protocol, the route of administration for the priming does not have to be the same route as used for the boosting. As described in Example 17, the prime may be administered parenterally and the boost may be administered transdermally.

The vaccine formulation may be administered with other agents including other adjuvants as well as immune stimulatory molecules including cytokines.

The following non-limiting examples are illustrative of the present invention:

EXAMPLES

Example 1

Obtaining a Washed Oil Body Preparation from Oilseed Rape, Soybean, Sunflower, White Mustard, Peanut, Squash, Flax, Safflower and Maize—Laboratory Scale.

Dry mature seeds obtained from *Brassica napus* cv Westar, soybean, sunflower, white mustard, peanut, squash, flax, safflower and maize were homogenized in five volumes of cold grinding buffer (50 mM Tris-HCl, pH 7.5, 0.4 M sucrose and 0.5 M NaCl) using a polytron operating at high speed. The homogenate was centrifuged at 10× g for 30 minutes in order to remove particulate matter and to separate oil bodies from the aqueous phase containing the bulk of the soluble seed protein. The oil body fraction was skimmed from the surface of the supernatant with a metal spatula and added to one volume of grinding buffer. In order to achieve efficient washing in subsequent steps it was found to be necessary to thoroughly redisperse the oil bodies in the grinding buffer. This was accomplished by gently homogenizing the oil bodies in grinding buffer using a polytron at low speed. Using a syringe, the redispersed oil bodies were carefully layered underneath five volumes of cold 50 mM Tris-HCl pH 7.5 and centrifuged as above. Following centrifugation, the oil bodies were removed and the washing procedure was repeated two times. The final washed oil body preparation was resuspended in one volume of cold Tris-HCl pH 7.5, redispersed with the polytron.

The oil body samples were dissolved in SDS sample buffer and then analyzed by SDS gel electrophoresis. The results are shown in FIG. 1.

The material thus obtained was then ready to be employed in various formulations.

Example 2

Obtaining a Washed Oil Body Preparation from Oilseed Rape, Sunflower and Maize on a Large Scale.

This example describes the recovery of the oil body fraction from canola, sunflower and maize seed on a large scale. The resulting preparation contains intact oil bodies and is comparable in purity with a preparation obtained using laboratory scale procedures.

Grinding of seeds.

A total of 10–15 kgs of dry canola seed (*Brassica napus* cv Westar), sunflower (*Helianthus annuus*) or maize (*Zea mays*) was poured through the hopper of a colloid mill (Colloid Mill, MZ-130 (Fryma); capacity: 500 kg/hr), which was equipped with a MZ-120 crosswise toothed rotor/stator grinding set and top loading hopper. Approximately 50–75 liters of water was supplied through an externally connected hose prior to milling. Operation of the mill was at a gap setting of 1 R, chosen to achieve a particle size less than 100 micron at 18° C. and 30° C. Following grinding of the seeds tap water was added to the seed slurry to a final volume of 90 liters.

Removal of solids.

The resulting slurry, was pumped into a decantation centrifuge (Hasco 200 2-phase decantation centrifuge maximum operating speed 6,000 rpm) after bringing the centrifuge up to an operating speed of 3,500 rpm. Transfer from the mill to the decantation centrifuge at a flow rate of 360 L/hr was achieved using a 1 inch M2 Wilden air operated double diaphragm pump. In 15–20 minutes approximately 15 kg of seed was decanted.

Oil body separation.

Separation of the oil body fraction was achieved using a Sharples Tubular Bowl Centrifuge model AS-16 (Alpha Laval) equipped with a three phase separating bowl and removable ring dam series; capacity: 150 L/hr; ringdam: 30 mm. Operating speed was at 15,000 rpm (13,200× g). A Watson-Marlow (Model 704) peristaltic pump was used to pump the decanted liquid phase (DL) into the tubular bowl centrifuge after bringing the centrifuge up to operating speed. This results in separation of the decanted liquid phase into a heavy phase (HP) comprising water and soluble seed proteins and a light phase (LP) comprising oil bodies. The oil body fraction which was obtained after one pass through the centrifuge is referred to as an unwashed oil body preparation. The oil body fraction was then passed through the centrifuge three more times. Between each pass through the centrifuge, concentrated oil bodies were mixed with approximately five volumes of fresh water. The entire procedure was carried out at room temperature. The preparations obtained following the second separation are all referred to as the washed oil body preparation. Following three washes much of the contaminating soluble protein was removed and the oil body protein profiles obtained upon SDS gel electrophoresis were similar in appearance to those obtained using laboratory scale procedures.

The large scale oil body preparation may be pasteurized. Pasteurization is achieved by initially thickening the washed oil bodies with centrifugation to a water content of 30 to 60%, preferable between 35 and 50% weight and most preferable between 37 and 40% weight. The thickened oil body solution can then be pasteurized in a constant temperature water bath at approximately 65° C. for 20 minutes. The pasteurization temperature could range between 50 and 90° C. and the time for pasteurization could range between 15 seconds to 35 minutes. If the oil bodies are used in a cosmetic formulation, then before pasteurization, 0.1% Glydant Plus, 0.1% BHA and 0.1% BHT may be added as a preservative and anti-oxidants respectively.

Example 3

Removal of Seed Proteins by Washing the Oil Body Phase.

This example describes the recovery of a washed oil body fraction from canola, maize and sunflower seed. Using different washing conditions, it is shown that the washes result in the removal of significant amounts of seed proteins from the oil body preparation. These proteins include proteins which might be allergenic.

A total of 10–15 kgs of dry canola seed (*Brassica napus* cv Westar), maize (*Zea mays*) or sunflower (*Helianthus annuus*) was poured through the hopper of a colloid mill (Colloid Mill, MZ-130 (Fryma)), which was equipped with a MZ-120 crosswise toothed rotor/stator grinding set and top loading hopper. Approximately 50–75 l water was supplied through an externally connected hose prior to milling. Operation of the mill was at a gap setting of 1 R, chosen to achieve a particle size less than 100 micron at 18° C. and 30° C. Following grinding of the seeds, tap water was added to the seed slurry to a final volume of 60–90 liters and a sample of the seed slurry was obtained for SDS gel electrophoresis. The slurry was then pumped into a decantation centrifuge (Hasco 200 2-phase decantation centrifuge maximum operating speed 6,000 rpm) after bringing the centrifuge up to an operating speed of 3,500 rpm. Transfer from the mill to the decantation centrifuge was achieved using a 1 inch M2 Wilden air operated double diaphragm pump. In 15–20 minutes approximately 15 kg of seed was decanted. A sample from the decanted liquid phase was obtained for SDS gel electrophoresis. Separation of the oil body fraction was achieved using a Sharples Tubular Bowl Centrifuge model AS-16 (Alpha Laval) equipped with a three phase separating bowl and removable ring dam series; capacity: 150 L/hr; ringdam: 29 mm. Operating speed was at 15, 000 rpm (13,200× g). A Watson-Marlowe (Model 704) peristaltic pump was used to pump the decanted liquid phase into the tubular bowl centrifuge after bringing the centrifuge up to operating speed. The unwashed oil body phase was obtained and mixed with approximately volumes of water. This procedure was repeated a total of three more times. The oil body phase which was obtained following the first spin, is referred to as an unwashed oil body preparation. All other preparations are washed oil body preparations. Samples for analysis by SDS gel electrophoresis were obtained following the first and fourth separations.

Upon completion of the fourth wash a 0.9 ml sample of the oil body preparation was homogenized in 0.1 ml 1 M $Na_2CO_3$ and left at room temperature for 30' with agitation. The washed oil body fraction was then recovered following centrifugation, washed once with water and prepared for SDS gel electrophoresis.

Figure 2:
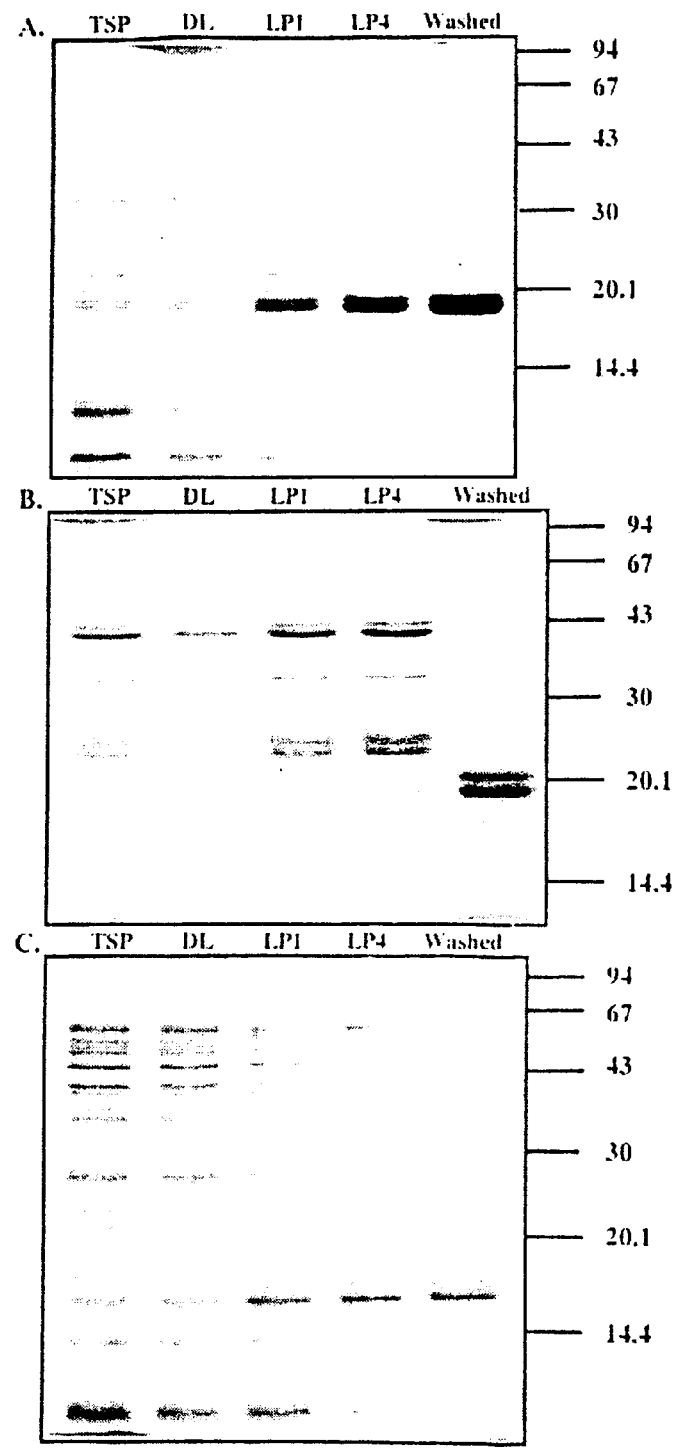
FIGS. 2A–C are Coomassie blue stained gels showing the protein profiles of various seed fractions obtained from *Brassica napus* (Canola) (A), sunflower (B), and maize (C). The gels show the following fractions (1) total seed protein (TSP), (2) decanted liquid phase (DL), (3) unwashed oil bodies (LP1), (4) three washes with water (LP4), (5) four washes with water and one wash with 100 mM $Na_2CO_3$ (Washed).

All of the samples were dissolved in SDS sample buffer and the samples were analyzed by SDS gel electrophoresis. The results are shown in FIG. 2.

Example 4

The Effect of Washing the Oil Body Phase on Water Retention Characteristics.

A washed oil body preparation and an unwashed oil body phase were prepared from rapeseed as in example 2. To determine the difference in water retention capacity between the unwashed oil body phase and the washed oil body preparation, 30 mls of oil body preparations were thoroughly mixed using a vortex. The preparations were then incubated for 2 hours in a water bath at 40, 60 or 80° C. and the samples were centrifuged at 1,500× g for 20 minutes (undiluted samples). Another set of samples was prepared by mixing 15 g of washed or unwashed oil body preparation with 15 ml of water. The samples were mixed on a vortex and then incubated at 40, 60 or 80° C. for 2 hours and the amount of water present in the samples was determined following centrifugation at 1,500× g for 20 minutes (diluted samples). Loss of mass attributable to evaporation was measured at 80° C. and 60° C.

At 80° C., the undiluted preparations comprising oil bodies lost significant amounts of water through evaporation. The preparation of unwashed oil bodies lost 26% of their mass, while the washed preparation lost 16%. Upon centrifugation the unwashed preparation released approximately 2.5 ml of aqueous phase, while the washed oil bodies remained in the same phase. Both diluted preparations absorbed water. The volume of oil bodies increased in both cases to 18.5±1 ml.

At 60° C., the undiluted preparations lost approximately 10% of water through evaporation. Following centrifugation, the washed preparation released about 0.5 ml of aqueous phase, while the washed oil body preparation stayed in the same phase. Both diluted preparations absorbed water. At 60° C., the volume of oil bodies increased in both cases to 18±1 ml.

At 40° C., the undiluted samples both released approximately 2 ml of aqueous phase. When the diluted samples were compared, the unwashed preparation absorbed about 3 ml of water, as was the case at 60 or 80° C. However the washed preparation absorbed 8 ml of water at 40° C.

These experiments demonstrate that in a washed oil body preparation heated to 60° C. or 80° C., water remains more tightly associated with the oil body preparation than in an unwashed preparation. When cooled down the washed oil body preparation appeared to be more stable than the unwashed emulsion. When heated to 40° C., the washed oil body preparation was able to absorb a larger volume of exogenously added water without resulting in phase separation offering greater flexibility in preparing oil body based formulations.

Example 5

The Effect of Washing Oil Bodies on Oil Absorption Characteristics.

A washed oil body preparation and an unwashed oil body phase were prepared from rapeseed as in example 2. To determine the difference in oil absorption capacity between the unwashed oil body phase and the washed oil body preparation, 2 grams of the oil body preparations were dispersed into 12 ml of refined, bleached, deodorized canola oil in a 50 ml tube. The contents were stirred for 30 seconds every 5 minutes for 30 min. The tubes were then centrifuged at 4,400 rpm for 25 min. The free oil was decanted and the percentage of absorbed oil was determined by weight difference. Three preparations of washed oil bodies were tested and three preparations of unwashed oil bodies were tested.

The oil absorption capacity of unwashed oil bodies was found to vary significantly between the three batches and varied from 18.7% to 28%. Washed oil bodies had reproducible oil absorption of 32±1%. Thus the washed oil body preparation was found to be superior since (1) a larger amount of oil was found to be absorbed and (2) the absorption occurred in a more reproducible manner.

Example 6

Modification of Native Oil-Bodies for Binding Antigens

In this example, the use of native oil-bodies derived from non-transgenic plants for antigen delivery is described. The isolated native oil-bodies were chemically modified to contain biotin molecules covalently linked to oil body proteins such as oleosins. These modified oil bodies are able to bind strepavidin-antigen complexes, thus providing a vaccine composition containing oil bodies, antigen and a strepavidin coupling moiety. To carry out the chemical modification of oil bodies, plant seeds from the oilseed plant *Brassica napus* were used for the isolation of oil-bodies. All procedures were performed under sterile conditions. Typically, 2–3 grams of mature seeds were first surface sterilized by treatment with 70% ethanol for 15 min at room temperature. The seeds were washed 2 to 3 times with sterile saline, then crushed in a pre-sterilized mortar with pestle using enough sterile saline to maintain liquid consistency. The crushed seed suspension was diluted to 40 mls with saline and transferred to a 50 ml polypropylene tube and centrifuged at 3500 rpm (10,000× g) for 30 minutes. The "fat pad" (containing the oil-bodies) was transferred to a 50 ml polypropylene containing 40 ml of sterile saline buffer and re-centrifuged. This washing step was repeated twice and then the final fat pad was re-suspended in small amount of sterile saline. Protein content was determined and the solution adjusted to a concentration of approximately 10 mgs oleosin (oil-body protein) per ml of solution. A total of 20 ul of the biotinylation reagent N-Hydroxysuccinimidobiotin (NHS-biotin), dissolved at a concentration of 12.5 mg/ml in dimethyl formamide was added per mg of oleosin. After mixing gently for 30 min to 1 hour, the biotinylated oil-bodies were centrifuged for 20 min and the undernatant removed. The biotinylated oil-bodies were resuspended in saline and recentrifuged. This wash was repeated and the fat layer resuspended in saline to a final concentration of 10 mg oleosin (oil-body protein) per ml. These modified oil-bodies are then used for coupling to strepavidin-antigen complexes.

Example 7

Production of Recombinant Antigens

A novel expression system for production of recombinant antigen was employed to produce antigen that is easily purified and contains a single biotin moiety at a selected region. The expression vector can be induced to express in *E. coli* and contains an T7 promoter and a region encoding an N-terminal biotin consensus sequence (Schatz, P. J. 1993. Use of peptide libraries to map the substrate specificity of a peptide-modifying enzyme: A 13 residue consensus peptide specifies biotinylation in *Escherichia coli*. Schatz, P., Bio/Technology 11:1138–1143), a polyhistidine segment and a multiple cloning site (MCS) to facilitate fusion in frame to foreign genes. The vector is referred to as pT7biohistag. The restriction map of this vector is shown in FIG. 7. Expression in *E. coli* from this vector containing a coding sequence inserted in-frame into the MCS results in a recombinant fusion protein that can readily be purified by metal-chelate chromatography due to the polyhistidine region. The recombinant protein also contains a biotin moiety attached to the lysine residue present in the N-terminal biotin consensus sequence, the biotinylation being carried out the BirA protein in the *E. coli* cells. It is noted that in some cases, particularly those cases where recombinant protein expression is very high in this system, the proportion of recombinant protein that is fully biotinylated may be reduced. Accordingly, in these instances, the purified protein can be fully biotinylated by the addition of biotin, ATP and a recombinant form of the BirA protein (Tsao, K. L., B. DeBarbieri, H. Michel, and D. S. Waugh. 1996. A versatile plasmid expression vector for the production of biotinylated proteins by site-specific, enzymatic modification in *Escherichia coli*. Gene 169:59–64). Recombinant antigen is produced in *E. coli* strain HMS174DE3 pLysS. Bacterial cells are grown and the expression of the recombinant gene induced by 0.5 mM IPTG, which causes the expression of the pT7biohistag vector. Following induction and growth for a period of time, cells are harvested, subjected to French press lysis, centrifuged to remove cellular debris and membranes and the antigen purified from the supernatant by nickel chelate affinity matrix chromatography. The purified antigen was fully biotinylated by incubation in the presence of a GST-BirA (glutathione-S-transferase) fusion protein with biotin and ATP added. The BirA was removed by a GST affinity chromatography column and the fully biotinylated antigen was repurified by metal chelate chromatography as above. This procedure allows for the production of recombinant antigen containing a biotin moiety.

Example 8

Coupling of Oil-Bodies and Antigens

In this example, biotinylated oil-bodies and biotinylated antigens were combined in the presence of strepavidin to form an oil-body-antigen complex. One mole of strepavidin can bind four moles of biotin, thus strepavidin can be used to link or couple the biotinylated antigen to the biotinylated oil-bodies. In order to couple the biotinylated antigen to the biotinylated oil-bodies, the biotinylated antigen was premixed with streptavidin and this mixture was then added to the biotinylated oil bodies. This stepwise coupling allows control of the amount of antigen that is coupled to the oil-body surface. As a control, adding a large excess of free biotin allows for the isolation of biotinylated oil-bodies without antigen attached. All preparations of antigen, streptavidin and oil-bodies were made in sterile saline. Non-particulate preparations were filter sterilized. Biotinylated antigen was combined with streptavidin (SA) at 2.5:1 molar ratio, then the antigen-SA complex was added to biotinylated oil-bodies, and mixed vigorously. The amount of antigen-SA complex added to the biotinylated oil-body was typically adjusted to emulate a 1–10% expression of oleosin fusion protein in a transgenic oil-body. Thus the antigen:oleosin molar ratio was 1.25:100 or 2.5:100 in most experiments and up to 1:10 in some experiments. The coupled oil-body-antigen-SA mixture was used for immunization of test animals.

Example 9

Production of an Oil-body—Antigen Complex Comprising a Recombinant Surface Antigen In this example, a representative surface antigen was cloned into the vector pT7biohistag and expressed. The transferrin binding protein B (TbpB) from *Neisseria meningitidis* was used as a representative surface antigen as it is a candidate for a vaccine for meningococcal meningitis (Danve, B., Lissolo, L., Guinet, F., Boutry, E., Speck, D., Cadoz, M., Nassif, X., and Quentin-Millet, M. J. Safety and immunogenicity of a *Neisseria meningitidis* group B transferrin binding protein vaccine in adults. Nassif, X., Quentin-Millet, M. -J., and Taha, M. -K. 53.98. Eleventh International Pathogenic Neisseria Conference). The coding region of the transferrin binding protein was isolated by PCR using primers that were modified to contain convenient restriction sites for cloning into the pT7biohistag vector. The resultant vector, called pT7BioHisM982TbpB was transformed into *E. coli*. The sequence of the cloned gene was confirmed by DNA sequencing, the restriction map is shown in FIG. 8. The *E. coli* strain containing the vector was grown to mid-log phase, antigen expression was induced and the recombinant antigen purified as described in Example 7. The recombinant antigen was fully biotinylated as described in Example 7, and coupled to biotinylated oil-bodies as described in Example 8. The TbpB-oil-body-strepavidin complex was used to immunize animals.

Example 10

Expression of an Antigen as an Oleosin Fusion in Oilseed Plants

In this example, we have prepared a transgenic plant, which expresses an oleosin-M982 TbpB N-lobe fusion that associates with oilbodies. The oil seed plant used in this example is *Arabidopsis thaliana*. A translation fusion between the oleosin 18 kDa and the coding region of M982 TbpB N-lobe under the control of a seed specific promoter was cloned into the binary vector pSBS2004. The resultant vector, pSBS2004-92 M982TbpB N-lobe is shown in FIG. 10 was used to transform *Agrobacterium tumefaciens* strain EHA101. The transformed Agrobacterium strain was then used to transformed *A. thaliana* (Bechtold, N., Ellis J., and Pelletier, G. 1993. In planta Agrobacterium-mediated gene transfer by infiltration of adult plants. C. R. Acad. Sci. Paris, Life Sciences 316:1194–1199). Infected plants were allowed to mature and set seeds. Putative transgenic seeds were sown onto appropriate germination media in the presence of the herbicide, phosphinothricin (PPT). Transgenic plants that survived selection were allowed to mature and set seeds. Transgenic oilbody expressing M982TbpB N-lobe as an oleosin fusion were isolated as described in Example 6. FIG. 9A shows is a Coomassie blue stained gel of transgenic oilbody proteins isolated from transgenic seeds expressing M982 TbpB N-lobe as an oleosin fusion. FIG. 9A shows that the oleosin-M982 TbpB fusion has an approximate molecular mass of 58.0 kDa. FIG. 9B shows a western blot of the SDS gel using antibodies against M982 TbpB. The figure shows that the oleosin-M982 TbpB N-lobe fusion can be recognized by the polyclonal antibody against M982 TbpB. In addition, M982TbpB N-lobe retains binding activity to human transferrin conjugated to horse radish peroxidase as shown in FIG. 10. The results show that a fusion comprising of an oleosin and M982 TbpB N-lobe can be expressed and targetted onto the surfaces of oilbodies of oil seed plants and that M982 tbpB N-lobe retains binding activity.

In addition, the present invention also used transgenic oilbodies expressing β-glucuronidase (GUS) as an oleosin fusion in *Brassica napus*. In this experiment, a fusion protein comprising the GUS (beta-glucuronidase) enzyme and a oleosin gene was used for immunizations. The recombinant gene, was inserted into plant cells, and transgenic plants obtained (Kuhnel, B., L. A. Holbrook, M. M. Moloney, and G. J. H. van Rooijen. 1996. Oil bodies of transgenic *Brassica napus* as a source of immobilized beta-glucuronidase. JAOCS 73:1533–1538). The resultant transgenic *Brassica napus* produces oil-bodies with the GUS enzyme on the surface of the oilbody. Transgenic oilbodies expressing GUS were isolated as described in Example 6 and used to immunized animals.

Example 11

Immunization of Animals using Oil-body-antigen Complexes

In this example, groups of female Balb/C mice (3 to 6 weeks of age) were immunized with oil-body-antigen complexes. The mice received two intraperitoneal injections of the antigen preparations two weeks apart and serum samples were obtained weekly by tail bleeds. Dilutions of the sera were analyzed for anti-TbpB antibodies by ELISA (enzyme linked immunosorbent assay) using immobilized recombinant TbpB. Bound antibodies were detected with an anti-murine IgG (gamma-specific) conjugate and appropriate substrate. The curves were compared to that obtained with a murine IgG standard of known concentration and anti-TbpB mouse sera from the VSA3-immunized mice (pooled) in order to determine the concentration of specific antibody in the sera. Mice (n=3/group) were injected with one of the following preparations:
(i) 10 µg of recombinant TbpB,
(ii) 10 µg of recombinant TbpB in 1:4 VSA3 adjuvant/saline (VSA3 is an optimal adjuvant used for experimental veterinary vaccination experiments e.g., Harland, R. J., et al. 1992. The effect of subunit or modified live bovine herpesvirus-1 vaccines on the efficacy of a recombinant Pasteurella haemolytica vaccine for the prevention of respiratory disease in feedlot calves. Can.Vet.J. 33:734–741),
(iii) 10 µg of recombinant TbpB protein coupled to a biotinylated oil-body preparation containing 200 µg of oleosin (1.25:100 molar ratio),
(iv) 10 µg of recombinant TbpB coupled to a biotinylated oil-body preparation containing 20 µg of oleosin (12.5:100 molar ratio),
(v) 10 µg of recombinant TbpB in an uncoupled oil-body preparation containing 200 µg of oleosin, and
(vi) 10 µg of recombinant TbpB in an uncoupled oil-body preparation containing 20 µg of oleosin.

The immune response of the animals, as measured by specific antibody levels to the TbpB are shown in Table 3.

The results demonstrate that the oil-body-strepavidin-TbpB complex provide a substantial increase in antibody response to TbpB compared to using the TbpB alone. Comparing the results to those obtained with 1:4 VSA3 suspension as adjuvant indicate that the oil-body-strepavidin-TbpB complex provides a similar response at four weeks. The results also demonstrate that the results with a lower ratio of biotinylated antigen to biotinylated oil-body do not reduce the immune response against antigen and may provide a greater adjuvant effect.

Example 12

Safety of Oil-Bodies in Systemic Immunization

In order for oil-bodies to be useful as a vaccine delivery system, administration of oil-bodies should not cause any undesired side effects such as acute toxicity or an adverse immune response. The parenteral (systemic) route of administration was chosen as the most likely to cause acute toxicity. The oil-bodies were prepared under sterile conditions essentially as described above. The final fat pad was re-suspended in sterile saline to a final protein concentration of 20 mg/ml. An aliquot of the suspension was subjected to SDS PAGE analysis to confirm the purity of the oil body preparation.

Rabbits were selected as the appropriate model as rabbits have been used for vaccine toxicity studies previously. The anticipated dosage required for vaccine applications was based on the expectation that the dose of antigen would be between 2 and 50 µg per injection for rabbits and that between 1 and 5% of the oleosin would be a fusion protein a transgenic seed. For a 50 kDa antigen, an anticipated vaccine dose (2–50 µg), would correspond to 0.4–10 µg of oleosin in the fusion protein. Thus an effective immunization dose would be 40 µg–1 mg total protein (oleosin) at 1% expression and 8 mg to 200 µg at 5% expression. Thus, 20 mg dose of oleosin per injection would represent a 20–100 fold higher dose than immunization. Eight healthy, adult female New Zealand white rabbits (approximately 2.5–3 kg) were injected with oil-bodies intramuscularly in the thigh (1 ml containing 20 mgs of oil-body protein) and subcutaneously in the dorsal neck area (1 ml containing 20 mgs of oil-body protein) on days 0, 14 and 28. Three control rabbits were injected with 1 ml normal saline in the same regions using the same schedule. The rabbits were monitored for body temperature and general state of health daily for the duration of the experiment. After the third injection, the rabbits were sacrificed and tissue samples were taken for histopathological analysis.

The treated rabbits did not develop any increase in body temperature (relative to control animals) or any physical signs of distress (change in fur texture, etc.). Histopathological analysis of the liver, spleen, heart and muscle did not reveal any pathophysiological changes. There were no residual pathophysiological features (i.e inflammatory infiltrate, scarring etc.) at the sites of injection. The results indicate that there are no acute signs of toxicity due to the systemic administration of plant-derived oilbodies at doses considerably higher than would ever be used for immunological purposes. In addition, the results demonstrate that there are no local or systemic pathophysiological changes from systemic administration of oilbodies.

To determine if there was an immune response to oleosin and see if this response interfered or reduced the response to specific antigens, sera from the mice in the Example 11 described above were tested for the antibody response to oleosin. Native oil-bodies were immobilized on hydrophobic protein-binding microtiter plates and EUSA performed as described above. Anti-oleosin antibody levels were calculated by comparison to the known murine IgG standard. Results are shown in Table 4.

These results show that the anti-oleosin antibody response is low, does not vary much regardless of the 10 fold increase in the dose for some groups over others (groups iv and vi over iii and v) and that the anti-oleosin response does not adversely affect the specific response to the specific antigen (TbpB responses in Example 11). Similarly, a low but non-interfering response was seen to streptavidin in mice that received antigen-coupled oil-bodies or antigen-streptavidin (results not shown). The animals treated with oil-bodies (either as a control or coupled to antigen) showed no morbidity (including no evidence of acute or delayed allergic response) or mortality. By comparison, initial experiments where a 1:3 VSA3 suspension was used resulted in 100% mortality in the treated mice. Accordingly the VSA3 adjuvant is not suitable for widespread use.

Example 13

Immunization of Animals with More Than one Antigen

In this example, multiple antigens were used in combination with coupling to oil-bodies. The C-terminal subfragment of tetanus toxoid (TTC) was used since it had been shown previously that the C-terminal subfragment was devoid of toxin activity yet retains its immunological properties and can be expressed as a recombinant protein in *E. Coli* (Halpern, J. L., W. H. Habig, E. A. Neale, and S. Stibitz. 1990. Cloning and expression of functional fragment C of tetanus toxin. Infect Immun. 58:1004–1009). The C-terminal fragment was cloned by PCR, inserted into the pT7biohistag vector and recombinant antigen purified as described in Example 7. The TbpB antigen was also used. Antigens were coupled to biotinylated oil-bodies as described in Example 8. In the experiment examining multiple antigens, groups of mice were immunized intraperitoneally 2 weeks apart with one of the following preparations:
(i) 10 µg of recombinant TTC coupled to a biotinylated oil-body preparation containing 200 µg of oleosin (n=4),
(ii) 10 µg of recombinant TTC and 10 µg of recombinant TbpB coupled to a biotinylated oil-body preparation containing 200 µg of oleosin (n=4).
(iii) 10 µg of recombinant TbpB coupled to a biotinylated oil-body preparation containing 200 µg of oleosin (n=4).

Serum samples were obtained biweekly by tail bleeds. Anti-TTC or anti-TbpB antibody levels were determined by ELISA using immobilized recombinant TTC or TbpB and appropriate standards as describe above. The results from the immunization experiments evaluating immunization with multiple antigens compare model oil-bodies containing TTC or TbpB alone to oil-bodies with both antigens. The results demonstrate that model oil-body preparations containing more than one antigen do not compromise the response against the individual antigens. In fact, the immune response against the individual antigens was increased when both antigens are present. The results are as shown in Table 5.

Example 14

Immunization with a Oil-Body Preparation Containing an Oleosin Recombinant Fusion In this experiment, an oil body preparation from a transgenic plant expressing the beta-glucuronidase (GUS) enzyme fused to oleosin was used for immunizations. A recombinant gene encoding oleosin and GUS, was inserted into plant cells, and transgenic plants obtained (Kuhnel, B., L. A. Holbrook, M. M. Moloney, and G. J. H. van Rooijen. 1996. Oil bodies of transgenic *Brassica napus* as a source of immobilized beta-glucuronidase. JAOCS 73:1533–1538). The resultant transgenic *Brassica napus* produces oil-bodies with the GUS enzyme on the surface of the oil-body. Another source of recombinant GUS enzyme was obtained by the use of the bacterial expression vector pT7BHGus which can express GUS enzyme in bacteria. The expressed GUS enzyme also contains the biotinylation peptide sequence and the polyhistidine tag, allowing for purification of the recombinant enzyme and coupling of the enzyme to biotinylation oil-bodies. The vector map of pT7BHGus is shown in FIG. 9. In the experiment using GUS as a model antigen, groups of mice were immunized by intraperitoneal injection 2 weeks apart with one of the following preparations:
(i) 10 µg of recombinant GUS (n=3),
(ii) 10 µg of recombinant purified GUS and 3 mg/ml (0.6 mg/dose) of alum (aluminum phosphate) (n=2),
(iii) 10 µg of recombinant biotinylated GUS in a coupled oil-body preparation containing 200 mg of oleosin (n=4),
(iv) a transgenic oil body preparation containing 200 mg of oleosin and approximately 10 mg of GUS (each n=4).

Serum samples were obtained biweekly by tail bleeds. Anti-GUS antibody levels were determined by ELISA using immobilized recombinant GUS and appropriate standards as describe above. The results of the experiment demonstrate that the response was similar between the oil-bodies where the recombinant antigen is produced as a fusion product with oleosin and where the antigen was coupled to the oil-bodies by the use of biotinylation (Table 6) Both oil-body preparations provide a substantial increase in antibody response to GUS compared to GUS alone. Comparing the results to those obtained with alum as adjuvant indicate that oil-bodies are a more effective adjuvant than alum. The results also demonstrate that the results with transgenic antigen oil-bodies are similar to those obtained with coupled antigen oil-bodies, indicating that the coupled antigen oil-bodies are functionally similar to the transgenic oil-bodies in systemic immunization experiments.

Example 15

Efficacy of Plant Oil-Bodies as a Delivery Vehicle for Mucosal Immunization (Prime and Prime/boost)

In order to evaluate the efficacy of mucosal administration of antigen, the intranasal route of immunization was used because it has been shown to be an effective site for mucosal immunization and does not face the same set of problems as oral immunizations. The oral/gastric route of administration was tested for comparison. The transferrin binding protein B (TbpB) from *Neisseria meningitidis* was used as the antigen and the cholera toxin beta subunit (CTB) was included as a potential targeting/immunomodulating protein to determine if coupling this protein to oil-bodies would enhance the immune response attained by mucosal immunization. For the mucosal preparations, all components were assembled as described in Examples 7 and 8 and the coupled oil-bodies were concentrated by centrifugation to reduce the volume and increase the consistency.

For the addition of CTB, it proved difficult to obtain workable quantities of biotinylated protein using the pT7BioHis standard expression system. Thus an alternative expression system was employed. This alternative system utilized the pMalc2 vector (Riggs, P. 1994. Expression and purification of maltose binding protein fusions., p. 16-6-1-16-6-14. In: F. M. Ausubel, R. Brent, R. E. Kingston, D. D. Moore, J. G. Seidman, J. A. Smith, and K. Struhl (eds.), Current Protocols in Molecular Biology. Wiley, N.Y.). The pMalc2 vector allows expression in *E. coli*, similar to the pT7BioHis vector, but also contains a maltose binding protein sequence at the N-terminus of the recombinant protein. The pMalc2 vector was modified to contain the biotinylation and polyhistidine coding regions contained in the pT7BioHis vector essentially as described in Example 8. The modified pMalc2 vector is referred to as pMalc2BioHis and provides a substitute for the pT7BioHis vector as a means to express recombinant proteins. The cholera toxin beta subunit gene was PCR amplified with Taq polymerase from a clinical isolate of Vibrio cholera. The PCR product contained XmnI and HindIII sites that allowed easy insertion into the pMalc2BioHis vector. The entire construct thus contained a recombinant coding region comprising the cholera toxin beta subunit, a biotinylation consensus peptide region, a polyhistidine region and a maltose binding protein region. This expression system was induced and the biotinylated recombinant antigen was produced. This protein could be readily isolated with metal chelate chromatography and could be coupled to biotinylated oil bodies with streptavidin.

In the mouse experiments using TbpB as a model antigen, biotinylated oilbodies coupled with TbpB or with TbpB plus CTB were used. Groups of 2–3 mice were immunized with one of the following preparations and routes. Sera were collected biweekly and tested for anti-TbpB antibodies as described above.

The results from the mouse experiments as shown in Table 7 demonstrated a relatively low systemic Anti-TbpB antibody response when the coupled biotinylated oil-body preparations were delivered by the intranasal (3 $\mu$g/ml at 4 weeks) or intragastric route (5 $\mu$g/ml at 4 weeks). The response was substantially enhanced when CTB was included in the oil-body preparations (64 and 7.3 mg/ml for intranasal and intragastric routes, respectively). Although mucosal administration of oil-bodies did not induce substantial levels of systemic antibody (prime and boost), it enhanced the immune response to subsequent parenteral immunization (259 and 139 mg/ml systemic IgG for in and ig, compared to 37 $\mu$g/ml 2 weeks after ip immunization). This indicates that the mucosal immunizations had effectively primed the immune system for subsequent parenteral immunization.

Example 16

Efficacy of Plant Oil-Bodies as a Delivery Vehicle for Transdermal Immunization (Prime and Prime/Boost)

This example demonstrates that antigen coupled oil-bodies applied transdermally results in an enhanced immune response against the test antigen. Since transdermal administration is more likely to produce an enhanced mucosal immune response, evaluation of both systemic and mucosal antibody production was conducted. Transdermal immunization in combination with systemic administration was tested to see whether transdermal immunization could effectively prime the immune system even if its induction of systemic or mucosal antibody was limited. The production of recombinant antigen and preparation of antigen coupled oil-bodies is essentially as described in Examples 7 & 8. To provide an oil-body preparation suitable for transdermal application, the antigen-coupled oil-bodies were suspended in a minimal volume of buffer so that the consistency of the oil-body suspension was like a cream or lotion. A higher dose of antigen (100 μg) and oil bodies (2 mg) were chosen for transdermal applications than with systemic administration. For transdermal application the antigen coupled oil-body preparations were applied to a 2 $cm^2$ shaved region on the back/neck/shoulder region of the mice. After application of the preparations, the mice were individually restrained in a custom device for 1 hour to prevent access to the back region. The mouse experiments used TbpB as a model antigen. Groups of 2–3 mice were immunized 2 weeks apart with one of the following preparations:

(i) 100 μg of recombinant TbpB (transdermal),
(ii) 100 μg of recombinant TbpB coupled to a biotinylated oil-body preparation containing 2 mg of oleosin (transdermal), or
(iii) 10 μg of recombinant TbpB (ip boost)
(iv) 10 μg of recombinant TbpB coupled to a biotinylated oil-body preparation containing 200 μg of oleosin (ip boost).
(v) Control groups included mice immunized with oil-bodies alone or PBS.

The mice were immunized by the transdermal or intraperitoneal route at week 0 and week 2 (as indicated below) and serum antibodies assessed at weeks 2, 4 and 8.

The results from these mouse experiments as shown in Table 8 demonstrate that the model oil-body preparations delivered by the transdermal route provide a low but detectable systemic (serum IgG) antibody response in contrast to administration of TbpB alone. It was particularly interesting to note that the serum antibody titre continued to rise up to 6 weeks after the last application (week 8 sample), suggesting that a more prolonged or sustained stimulation of the immune system was occurring. It clearly indicates that this route of administration shows considerable promise and that varying the timing and number of applications may provide an opportunity to further optimize the immune response.

In addition, transdermal administration of model oil bodies appeared to prime the immune system for subsequent parenteral immunization. Thus the response at Week 4 for the td/ip group (445 μg/ml) was substantially greater than that for the ip/ip group at Week 2 (37 μg/ml), both of which correspond to 2 weeks after the first parental immunization.

Example 17

Efficacy of Plant Oil-bodies as a Delivery Vehicle for Mucosal and Transdermal Booster Immunization From the previous example, it appears that it may be valuable to examine combinations of routes of administration that might have useful application. For example, transdermal immunization may prove to be an effective means of boosting an initial parenteral immunization, which may have considerable appeal for human vaccine applications. To address this approach, groups of Balb/C mice (n=5) were given a primary subcutaneous (sc) injections of recombinant GUS protein in alum (10 μg GUS). Boosts followed at 4, 6, and 8 weeks using GUS-coupled oil-bodies (100 mg GUS, 2 mg oleosin) by either the intranasal or transdermal routes as described above. Sera were collected at weeks 4, 6, 8, and 11 following the sc primary immunization and tested for systemic anti-GUS antibodies by ELISA as described above.

The data in Table 9 suggest antigen-coupled oil-bodies may be particularly useful for booster immunizations following a systemic primary immunization by the presently approved adjuvant alum. The usefulness of antigen-coupled oil-bodies for use as a human booster vaccine strategy has several potential advantages. Transdermal or intranasal routes are non-invasive compared to systemic administration, thus patient compliance can be achieved more readily, particularly with parental concerns about the more invasive booster injections. In addition, the easy of application, particularly of the transdermal formulation, may lead to self administration of boosters via a take-home lotion or moist patch for application at set dates. This would greatly reduce costs to the health care system overall by negating several visits to physician offices for boosters. Finally, such a vaccine formulation may be given repeatedly over a longer period, which may lead to higher antibody levels because of the sustained exposure to antigen.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Room Temperature

| Time (days) | Color | Odor | Stability | Viscosity (cps) | Microbial Growth |
|---|---|---|---|---|---|
| 0 | Pale yellow | Very Mild | No separation | 3500 ± 100 | 500 |
| 14 | Pale yellow | No change | No separation | 3500 ± 100 | 300 |
| 25 | Pale yellow | No change | No separation | 3500 ± 100 | <10 |

45° C.

| 0 | Pale yellow | Very Mild | No separation | 3500 ± 100 | 500 |
| 14 | Pale yellow | Mild | No separation | 4000 ± 100 | <20 |
| 25 | Mildly yellow | Mild | No separation | 4000 ± 100 | <10 |

4° C.

| 0 | Pale yellow | Very Mild | No separation | 3500 ± 100 | 500 |
| 14 | Pale yellow | Very Mild | No separation | 3500 ± 100 | 250 |
| 25 | Pale yellow | Very Mild | No separation | 3500 ± 100 | <10 |

TABLE 2

Room Temperature

| Time (days) | Color | Odor | Stability | Viscosity (cps) | Microbial Growth |
|---|---|---|---|---|---|
| 0 | Dark yellow | Very Mild | Separation | Approx. 4000 | <20 |
| 14 | Dark yellow | Very Mild | Total Separation | Sluggish | <20 |
| 25 | Darker yellow | Very Mild | Total Separation | Sluggish | <10 |

45° C.

| 0 | Dark yellow | Neutral | No separation | 3500 ± 100 | <20 |
| 14 | Brown | Amine Odor | No separation | 4000 ± 100 | <10 |
| 25 | Dark brown | Fishy | No separation | 4000 ± 100 | <10 |

4° C.

| 0 | Dark yellow | Neutral | Separation | Approx. 4000 | <20 |
| 14 | Dark yellow | Neutral | No separation | 3500 ± 100 | <10 |
| 25 | Dark yellow | Neutral | No separation | 3500 ± 100 | <10 |

TABLE 3

Antibody levels following immunization with TbpB antigen and oil-bodies

| | Anti-TbpB (mg/ml) | | | |
|---|---|---|---|---|
| Immunogen | Week 1 | Week 2 | Week 3 | Week 4 |
| (i) TbpB alone | 21 | 39 | 750 | 1262 |
| (ii) TbpB plus VSA3 | 50 | 124 | 4471 | 2480 |
| (iii) TbpB coupled to oilbodies | 154 | 79 | 2685 | 2834 |
| (iv) TbpB coupled to oilbodies2 | 142 | 71 | 3056 | 2290 |
| (v) TbpB - mix[1] | 149 | 78 | 926 | 990[3] |
| (vi) TbpB - mix[1,2] | nd | 34 | nd | 554[3] |

[1]Oil-body preparation using biotin to prevent coupling of antigen/SA to biotinylated oil bodies.
[2]With a molar ratio of TbpB to oleosin of approximately 1/100 instead of 1/10.
[3]Responses significantly lower than model oil-body preparation by Student's T test.
nd - not determined.

TABLE 4

Oleosin antibody levels following immunization with oil-bodies

| | Anti-Oleosin (µg/ml) | |
|---|---|---|
| Immunogen | Week 2 | Week 4 |
| (i) TbpB alone | 0 | 0 |
| (ii) TbpB plus VSA3 | 0 | 0 |
| (iii) TbpB coupled to oilbodies | 13 | 68 |
| (iv) TbpB coupled to oilbodies2 | 25 | 84 |
| (v) TbpB - mix[1] | 6 | 67 |
| (vi) TbpB - mix[1,2] | 12 | 73 |

[1]Oil body preparation using biotin to prevent coupling of antigen/SA to biotinylated oil bodies.
[2]With a molar ratio of TbpB to oleosin of approximately 1/100 instead of 1/10.

TABLE 5

Antibody levels following immunization with multiple antigens

| | Specific Ab Level (mg/ml) | | | |
|---|---|---|---|---|
| | anti-TTC | | anti-TbpB | |
| Immunogen | Week 2 | Week 4 | Week 2 | Week 4 |
| TTC coupled to oil-bodies | 59 | 690 | <3 | <3 |
| TbpB coupled to oil-bodies | <3 | <3 | 48 | 404 |
| TTC/TbpB coupled to oil-bodies | 52 | 930 | 497 | 1476 |

TABLE 6

Antibody levels following immunization with GUS protein

| | Anti-GUS (mg/ml) | |
|---|---|---|
| Immunogen | Week 2 | Week 4 |
| GUS | 4 | 38 |
| GUS plus alum | 8 | 97 |
| GUS coupled to oil-body | 13 | 153 |
| GUS transgenic oil-body | 17 | 159 |

TABLE 7

Routes Used for Mucosal Immunization

| Primary Dose (TbPB-coupled oil-body preparation | Route | W or w/o 100 μg CTB | Secondary Dose (TbpB-coupled oil-body preparation) | Route | W or w/o 100 μg CTB |
|---|---|---|---|---|---|
| 50 μg/1000 μg | in | W/o | 10 μg/200 μg | ip | W/o |
| 50 μg/1000 μg | in | W/o | 50 μg/1000 μg | in | W/o |
| 50 μg/1000 μg | in | W | 10 μ/200 μg | ip | W/o |
| 50 μg/1000 μg | in | W | 50 5 g/1000 μg | in | W |
| 50 μg/1000 μg | ig | W/o | 10 μg/200 μg | ip | W/o |
| 50 μg/1000 μg | ig | W/o | 50 μg/1000 μg | ig | W/o |
| 50 μg/1000 μg | ig | W | 10 μg/200 μg | ip | W/o |
| 50 μg/1000 μg | ig | W | 50 μg/1000 μg | ig | w | in - intranasal; ig - gastric (via intragastric tube); ip - intraperitoneal

TABLE 8

Antibody levels following transdermal immunization with TbpB Immunogen Route of

| | | Anti-TbpB (mg/ml) | | |
|---|---|---|---|---|
| Immunization | | Week 2 | Week 4 | Week 8 |
| TbpB | td/td | <3 | 5 | 3 |
| | td/ip | 3 | 241 | 58 |
| | ip/ip | 19 | 928 | 345 |

TABLE 8-continued

Antibody levels following transdermal immunization with TbpB Immunogen Route of

| | | Anti-TbpB (mg/ml) | | |
|---|---|---|---|---|
| Immunization | | Week 2 | Week 4 | Week 8 |
| TbpB-coupled oil-bodies | td/td | 4 | 11 | 69 |
| | td/ip | <3 | 445 | 131 |
| | ip/ip | 37 | 1096 | 1241 |

TABLE 9

Antibody levels following intranasal/transdermal boosts with GUS protein

| | | Anti-GUS in mg/ml | | | |
|---|---|---|---|---|---|
| Immunogen | Route | Week 4 | Week 6 | Week 8 | Week 11 |
| GUS-coupled oil bodies | sc/td | 75 | 75 | 98 | 195[1] |
| GUS-coupled oil bodies | sc/in | 75 | 36 | 63 | 121[1] |
| GUS | sc/td | 75 | 2 | 6 | 62 |
| GUS | sc/in | 75 | 2 | 17 | 2[2] |
| GUS | sc/– | 75 | 9 | 17 | 24* |

SC on week 0 followed by td or in boosts on weeks 4, 6, and 8.
[1]Significantly increased over *GUS sc/–.
[2]Not significantly lower than *GUS sc/–.

---

We claim:

1. An immunogenic formulation comprising (a) an emulsion comprising substantially intact, washed oil bodies obtained from plant seeds, and (b) an antigen.

2. The immunogenic formulation according to claim 1 wherein said antigen is associated with the oil bodies.

3. The immunogenic formulation according to claim 2 wherein said antigen and said oil bodies are biotinylated and associated with each other through streptavidin.

4. The immunogenic formulation according to claim 1 wherein said antigen is prepared as a recombinant fusion protein with an oil body protein.

5. The immunogenic formulation according to claim 1 wherein the oil bodies are obtained from a plant selected from the group consisting of rapeseed (Brassica spp.), soybean (*Glycine max*), sunflower (*Helianthus annuus*), oil palm (*Elaeis guineeis*), cottonseed (Gossypium spp.), groundnut (*Arachis hypogaea*), coconut (*Cocus nucifera*), castor (*Ricinus communis*), safflower (*Carthamus tinctorius*), mustard (Brassica spp. and *Sinapis alba*), coriander (*Coriandrum sativum*), squash (*Cucurbita maxima*), linseed/flax (*Linum usitatissimum*), Brazil nut (*Bertholletia excelsa*), jojoba (*Simmondsia chinensis*) and maize (*Zea mays*).

6. A method for preparing an immunogenic emulsion formulation comprising:
    (1) obtaining substantially intact oil bodies form a plant cell;
    (2) washing the oil bodies to obtain a washed oil body preparation;
    (3) formulating the washed oil body preparation into an emulsion; and
    (4) adding an antigen.

7. The method according to claim 6 wherein said antigen is associated with the oil bodies.

8. The method according to claim 7 wherein said antigen and said oil bodies are biotinylated and associated with each other through streptavidin.

9. The method for preparing an immunogenic emulsion formulation according to claim 6 comprising:
    (1) obtaining oil bodies from plant seeds by a method that comprises:
        (a) grinding plant seeds to obtain ground seeds comprising substantially intact oil bodies
        (b) removing solids from the ground seeds; and
        (c) separating the oil body phase from the aqueous phase;
    (2) washing the oil body phase to yield a washed oil body preparation;
    (3) formulating the washed oil body preparation into an emulsion; and
    (4) adding an antigen.

10. A method of eliciting an immune response comprising administering an effective amount of an immunogenic formulation comprising (a) an emulsion comprising substantially intact, washed oil bodies obtained from plant seeds, and (b) an antigen to an animal in need thereof.

11. The method according to claim 10 wherein the immunogenic formulation is prepared according to a method comprising the following step:
    (1) obtaining substantially intact oil bodies form a plant cell,
    (2) washing the oil bodies to obtain a washed oil body preparation;
    (3) formulating the washed oil body preparation into an emulsion; and
    (4) adding an antigen.

12. The method according to claim 10 wherein the immunogenic formulation is administered orally, topically, or parenterally.

13. The method according to claim 10 wherein the immunogenic formulation elicits a cellular immune response.

* * * * *